(12) United States Patent
Hogenkamp et al.

(10) Patent No.: US 7,825,278 B2
(45) Date of Patent: Nov. 2, 2010

(54) SUBSTITUTED ENAMINONES, THEIR DERIVATIVES AND USES THEREOF

(75) Inventors: Derk J. Hogenkamp, Carlsbad, CA (US); Timothy B. C. Johnstone, Costa Mesa, CA (US); Kelvin W. Gee, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 1440 days.

(21) Appl. No.: 11/123,597

(22) Filed: May 5, 2005

(65) Prior Publication Data
US 2008/0064748 A1 Mar. 13, 2008

Related U.S. Application Data

(60) Provisional application No. 60/569,465, filed on May 6, 2004.

(51) Int. Cl.
| | |
|---|---|
| C07C 233/00 | (2006.01) |
| C07C 307/00 | (2006.01) |
| C07C 229/00 | (2006.01) |
| C07D 317/00 | (2006.01) |
| C07D 261/00 | (2006.01) |
| C07D 249/00 | (2006.01) |
| A61K 31/165 | (2006.01) |
| A61K 31/18 | (2006.01) |
| A61K 31/42 | (2006.01) |
| A61K 31/36 | (2006.01) |
| A61K 31/41 | (2006.01) |
| A61K 31/24 | (2006.01) |

(52) U.S. Cl. .............................. 564/163; 564/86; 560/35; 549/439; 548/246; 548/264.8; 514/377; 514/383; 514/466; 514/603; 514/609

(58) Field of Classification Search ................ None
See application file for complete search history.

(56) References Cited

FOREIGN PATENT DOCUMENTS

| EP | 371876 | 6/1990 |
| ES | 2049640 | 4/1994 |
| WO | WO 98/43964 | 10/1998 |

OTHER PUBLICATIONS

Database CAPLUS on STN, Acc. No. 1980:41916, Grohe et al., DE 2808070 (Aug. 30, 1979) (abstract).*
Database CAPLUS on STN, Acc. No. 1976:577306, Denzel et al., Archiv der Pharmazie (1976), 309(6), p. 486-503 (abstract).*
Braga et al., Chem. Commun. (2005), 29, p. 3635-3645.*
Burgers Medicinal Chemistry and Drug Discovery 5$^{th}$ ed., vol. I, (1995), Manfred E. Wolff ed., John Wiley & Sons, NY, p. 975-977.*
Modern Pharmaceutics 3$^{rd}$ ed., (1996), Gilbert S. Banker et al. ed., Marcel Dekker, Inc., NY, p. 596.*
Sayyed et al., Database CAPLUS on STN, Acc. No. 2000:429756, "An efficient synthesis of N-alkyl-1,4-dihydro-4-oxo-3-quinolinecarboxylic acids via ethyl 2-(2,2,2-tricholoroethylidene)-3-oxo-3-(2-chlorophenyl)propionate". Synthetic Communications (2000), vol. 30, No. 14, pp. 2533-2540.

Anders A. Jensen, Bente Frølund, Tommy Lijefors, and Povl Krogsgaard-Larsen,. "Neuronal Nicotinic Acetylcholine Receptors: Structural Revelations, Target Identifications, and Therpeutic Inspirations", Journal of Medicinal Chemistry, 2005; vol. 48; Num. 15, pp. 4705-4745.
W. Sieghart and M. Ernst, "Heterogeneity of GABa Receptors: Revived Interest in the Development of Subtype-Selective Drugs", Curr. Med. Chem—Central Nervous System Agents, 2005, 5(3); 217-242.
Povl Krogsgaard-Larsen, Bente Frølund, Flemming S. Jøgensen and Arne Schousboe; "GABAa Receptor Agonists, Partial Agonists, and Antagonists. Design and Therapeutic Prospects," Journal of Medicinal Chemistry, 1994, vol. 37, No. 16; pp. 2489-2505.
Derk J. Hogenkamp, Timothy B.C. Johnstone, Jin-Chen Huang, Wen-Yen Li, Minhtam Tran, Edward R. Whittemore, Rudy E. Bagnera, and Kelvin W. Gee, "Enaminone Amides as Novel Orally Active GABAa Receptor Modulators", J. Med Claim 2007, 50, 3369-3379.
Ramin Faghih, Murali Gopalakrishnan, and Clark A. Briggs, "Allosteric Modulators of the Alpha 7 Nicotinic acetylcholine Receptor," Journal of Medicinal Chemistry, 2008, vol. 51, No. 4, pp. 701-712.
Translation of "Decision to Grant a Patent of Invention," Ukrainian Patent Application No. a 200612755, filed May 5, 2005.
State Intellectual Property Office of P.R.C., Notice of the First Office Action; Serial No. 200580021414.1, filed May 5, 2005.
Communication Pursuant to Article 94(3) EPC, European Patent Office; Application No. 05 750 6438-1216, dated Jul. 29, 2008.
Sayyed, I.A., et al., "An efficient synthesis of N-alkyl-1,4-dihydro-4-oxo-3-quinolinecarboxylic acids via ethyl 2-(2,2,2-trichlorethylidene)-3-oxo-3-(2-chlorophenyl) propionate" Synthetic Communications, 30(14), 2533-2450 CIDEB SYNCAV; ISSN: 0039-7911, 2000 xp08076153.
Australian Patent Office Search Report and Written Opinion dated Oct. 3, 2008, for Application No. SG-200607693-9, filed May 5, 2005.
Singapore Search Report and First Written Opinion; Application No. 200607693-9; Dated Oct. 3, 2008.
Communication from the European Patent Office dated Mar. 19, 2007 re Application No. 05750643.8 and Supplementary Partial European Search Report.

* cited by examiner

Primary Examiner—Brian J Davis
(74) Attorney, Agent, or Firm—Cooley LLP

(57) ABSTRACT

The invention relates to substituted enaminones of Formula I and their derivatives and the discovery that these compounds modulate the effect of γ-aminobutyric acid (GABA) on the $GABA_A$ receptor complex in a therapeutically relevant fashion and may be used to ameliorate CNS disorders amenable to modulation of the $GABA_A$ receptor complex.

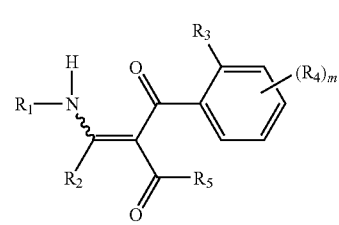

25 Claims, 5 Drawing Sheets

Figure 1. Dose response of ethyl 2-chloro-α-[[(4-ethynylphenyl)amino]methylene]-β-oxo-benzenepropionate, α-[[(4-ethynylphenyl)amino]methylene]-2-chloro-β-oxo-N-propyl-benzenepropanamide, 5α-pregnan-3α-ol-20-one, and clonazepam on 0.2 nM [$^3$H]flunitrazepam binding in rat cortex.
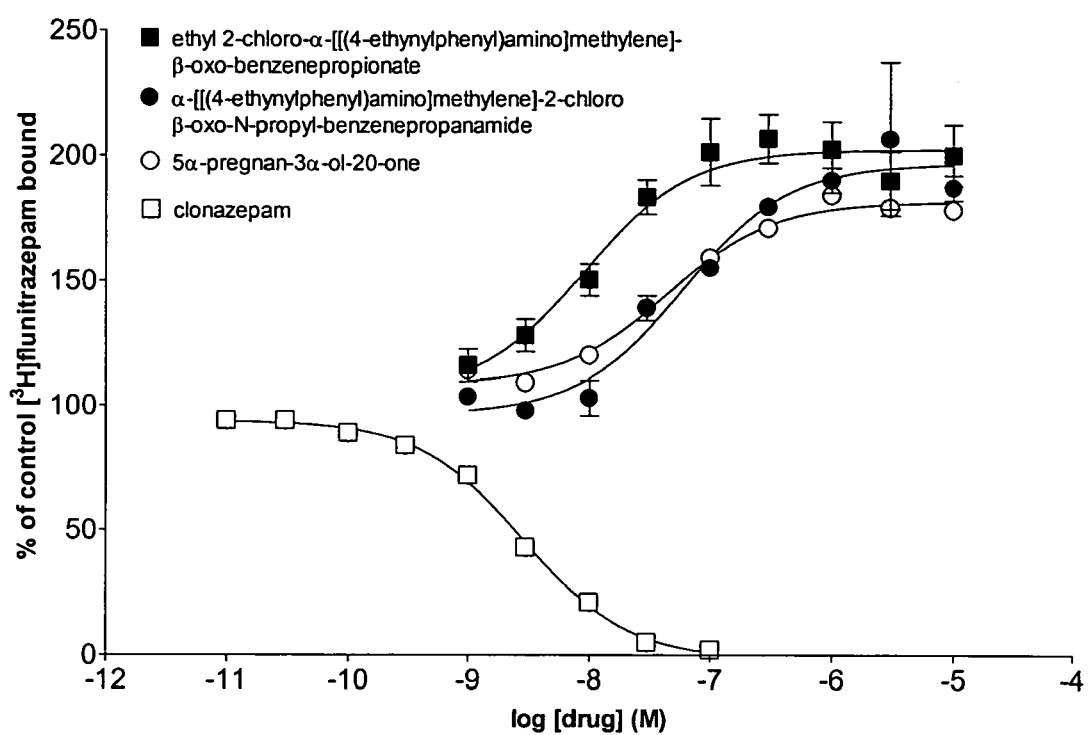

Figure 2: Dose response of 5α-pregnan-3α, 20α-diol in the absence and presence of 30 nM ethyl 2-chloro-α-[[(4-ethynylphenyl)amino]methylene]-β-oxo-benzenepropionate or 100 nM α-[[(4-ethynylphenyl)amino]methylene]-2-chloro-β-oxo-N-propyl-benzenepropanamide on 2 nM [$^{35}$S]TBPS binding in rat cortex.
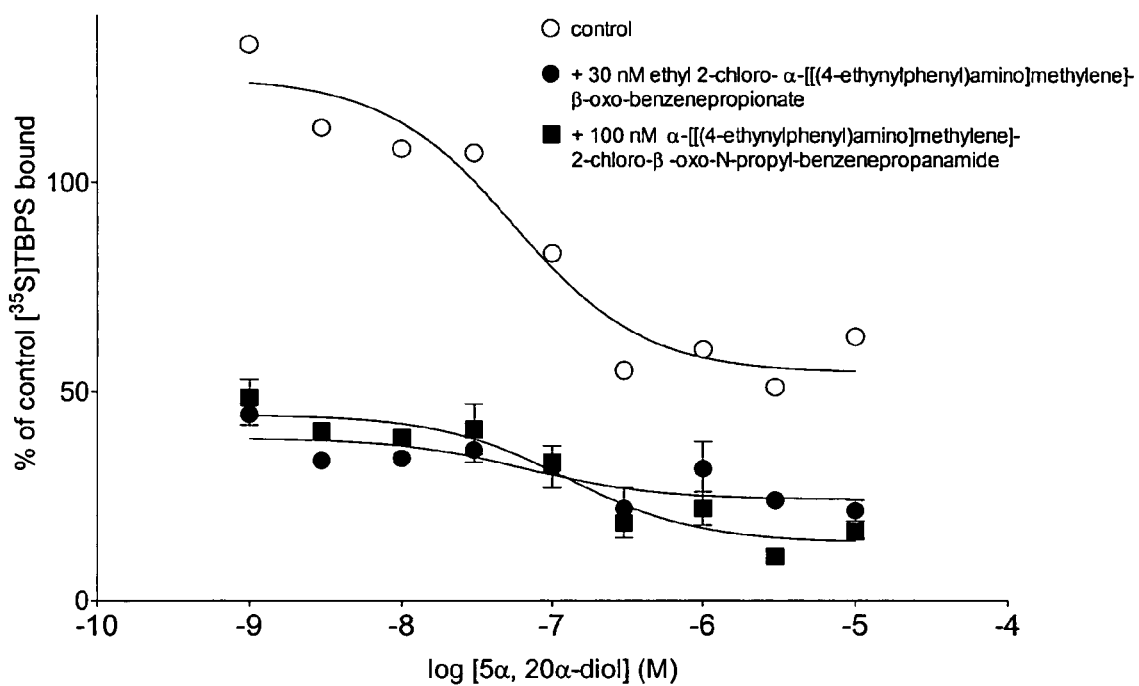

Figure 3: Dose response of ethyl 2-chloro-α-[[(4-ethynylphenyl)amino]methylene]-β-oxo-benzenepropionate, α-[[(4-ethynylphenyl)amino]methylene]-2-chloro-β-oxo-N-propyl-benzenepropanamide, and γ-aminobutyric acid on 5 nM [$^3$H]muscimol binding in rat cortex.
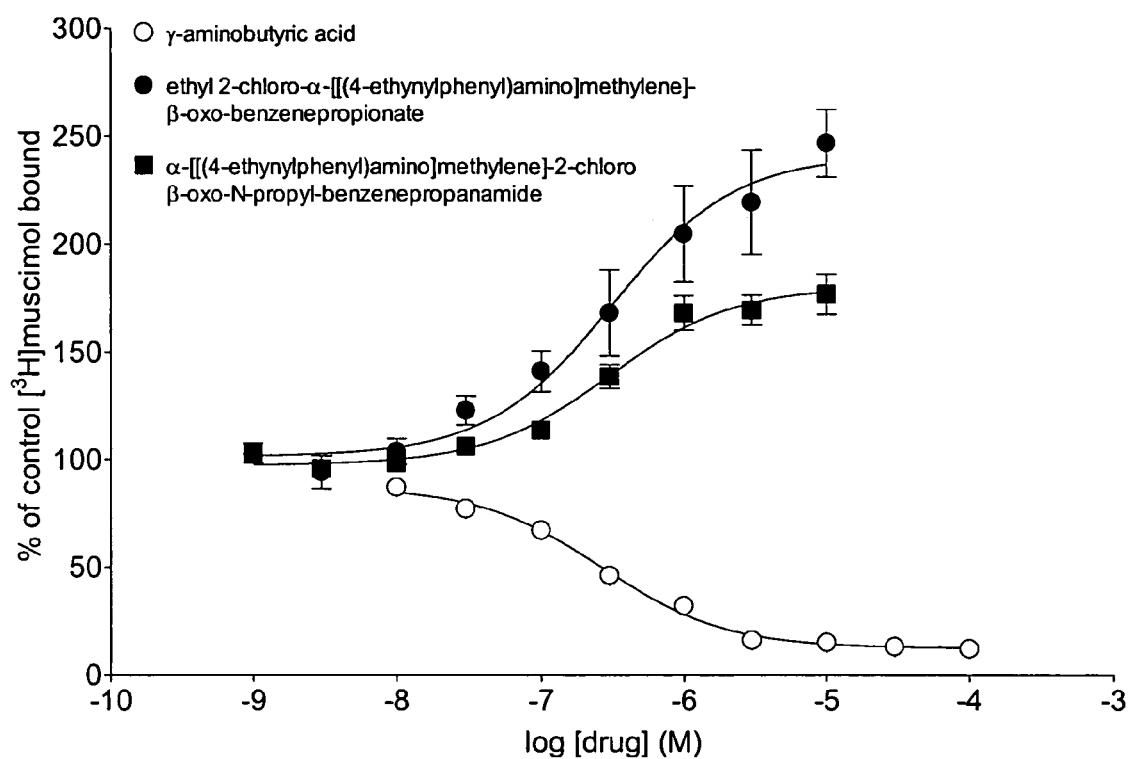

Figure 4. Dose response of loreclezole in the presence and absence of 300 nM ethyl 2-chloro-α-[[(4-ethynylphenyl)amino]methylene]-β-oxo-benzenepropionate on 0.2 nM [$^3$H]flunitrazepam binding in rat cortex.
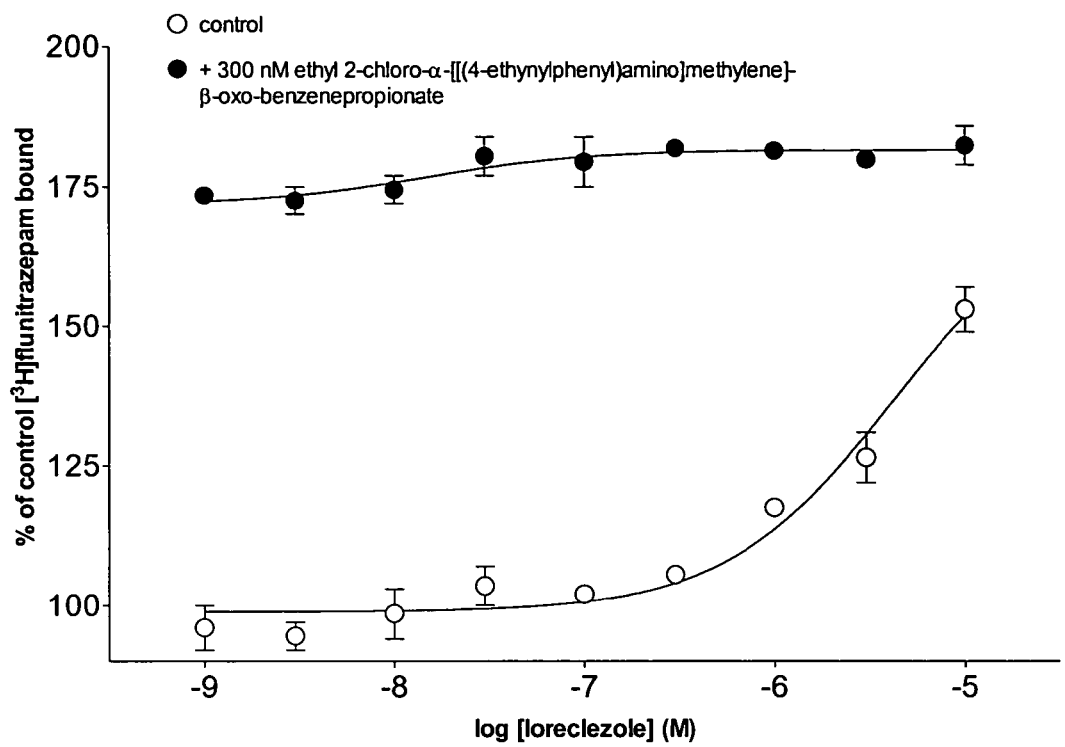

Figure 5. Dose response of pentobarbital in the presence and absence of 300 nM ethyl 2-chloro-α-[[(4-ethynylphenyl)amino]methylene]-β-oxo-benzenepropionate on 0.2 nM [$^3$H]flunitrazepam binding in rat cortex.
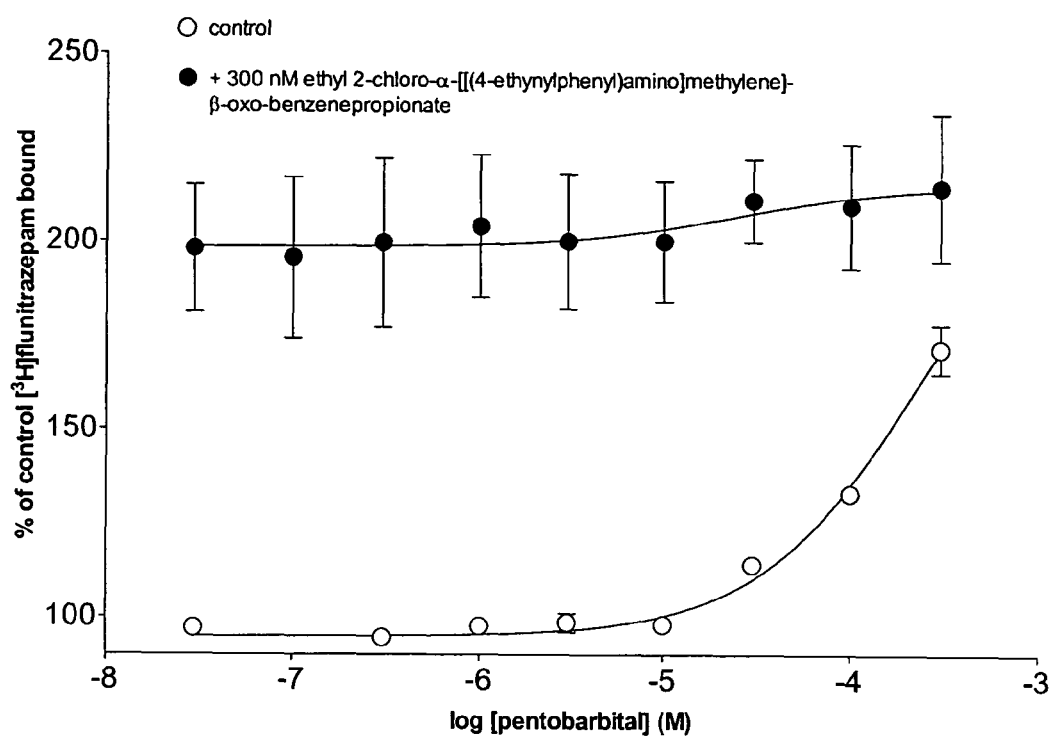

SUBSTITUTED ENAMINONES, THEIR DERIVATIVES AND USES THEREOF

This application claims the benefit of U.S. Provisional Application No. 60/569,465, filed May 6, 2004, the subject matter of which is incorporated herein in its entirety.

FIELD OF THE INVENTION

This invention is in the field of medicinal chemistry. In particular, the invention relates to substituted enaminones and their derivatives and the discovery that these compounds modulate the effect of γ-aminobutyric acid (GABA) on the $GABA_A$ receptor complex in a therapeutically relevant fashion and may be used to ameliorate CNS disorders amenable to modulation of the $GABA_A$ receptor complex.

BACKGROUND OF THE INVENTION

GABA is the most abundant inhibitory neurotransmitter in the mammalian brain. GABA controls brain excitability by exerting inhibitory functions on neuronal membranes by altering their permeability to specific ions. Binding of GABA to the $GABA_A$-type ($GABA_A$) receptor increases the permeability of neuronal membranes to chloride ions (Cl⁻). In most neurons the relative Cl⁻ ion concentration is greater outside than inside the membrane. Thus, selective permeability to Cl⁻ initiated by GABA binding forces Cl⁻ into the cell. The majority of fast inhibitory synaptic transmission is a result of GABA binding to the $GABA_A$ receptors. $GABA_A$ receptors are ubiquitously expressed throughout the CNS with almost all neurons staining for their presence. The $GABA_A$ receptor is a hetero-pentameric protein structure of the nicotinic acetylcholine receptor superfamily. Native $GABA_A$ receptors are formed from at least 19 related subunits. The subunits are grouped into α, β, δ, ε, π, and ρ families. The most prevalent combination of $GABA_A$ receptors is a stoichiometric combination of the 2×α, 2×β, and 1×γ subunits, with the remaining subunits relegated to substituting for the y subunit during specific development expression or in highly specific brain region localization. The adult brain predominately expresses the $\alpha_1\beta_2\gamma_2$ subunit combination (60%) with the $\alpha_2\beta_3\gamma_2$ and $\alpha_3\beta_n\gamma_2$ subunits comprising the majority (35%) of the remaining receptors. The relative effects of GABA are influenced by the receptor subunit expressed in a specific brain region or neuronal circuit.

The neurophysiological effects of GABA result from a conformational change that occurs when GABA binds to the $GABA_A$ receptor. The $GABA_A$ receptor and the associated ion channel complex (GRC) recognize many compounds that allosterically enhance the ability of GABA to bind to the $GABA_A$ receptor. The allosteric modulators have distinct sites on the GRC. These sites are separate and unique from the site that recognizes GABA. The most widely studied and characterized class of allosteric modulator of the GRC are those that interact with the benzodiazepine(BZ)-site.

Alternative sites for modulating the GRC have been described. For example, neuroactive steroids are non-hormonal steroids that bind and functionally modulate the GRC. The current role of neuroactive steroids in $GABA_A$ receptor pharmacology is supported by overwhelming evidence. Electrophysiological and biochemical techniques have confirmed the capacity of neuroactive steroids to allosterically modulate the GRC through a unique site of action. Experimentally, neuroactive steroids exhibit a pharmacological profile similar, but not identical, to the benzodiazepines. Neuroactive steroids have anxiolytic, anticonvulsant, and sedative-hypnotic properties.

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs) such as Valium) produce their therapeutically useful effects by interacting with specific modulatory sites on the GRC receptor complex.

RELATED ART

Sayyed, I. A. et al. (Synthetic Comm. 2000, 30(14), 2533) disclose the synthesis of the following compound as a synthetic intermediate:

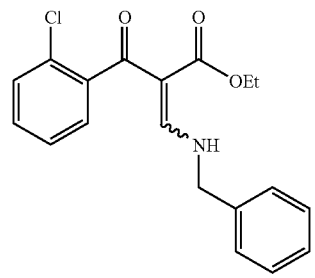

Palomo Coll, A. in Spanish patent 2049640 (1994) discloses the following compound as a synthetic intermediate:

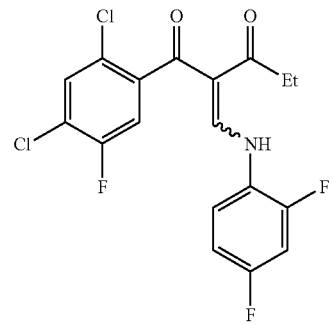

SUMMARY OF THE INVENTION

The present invention is related to the discovery that certain substituted enaminones represented by Formula I act as enhancers of GABA-facilitated Cl⁻ flux mediated through the $GABA_A$ receptor complex (GRC).

The invention is related to treating disorders responsive to enhancement of GABA action on GABA receptors in a mammal by administering an effective amount of a compound of Formula I as described herein.

The compounds of the present invention, being ligands for $GABA_A$ receptors, are therefore of use in the treatment and/or prevention of a variety of disorders of the central nervous system (CNS). In one aspect, the compounds are useful for the treatment and/or prevention of disorders of the CNS involving neuronal hyperexcitability. Such disorders include but are not limited to anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder, neuroses, convulsions, migraine, and depressive or bipolar disorders, for example single-episode or recurrent major depressive disorder, dysthymic disorder, bipolar I and bipolar II manic disorders, and cyclothymic disorder.

Another aspect of the present invention is directed to the use of the compounds of Formula I as enhancers of GABA-facilitated CL⁻ flux mediated through the $GABA_A$ receptor complex. Also, an aspect of the present invention is to provide a pharmaceutical composition useful for treating disorders responsive to the enhancement GABA-facilitated Cl⁻ flux mediated through the GRC, containing an effective amount of a compound of Formula I in a mixture with one or more pharmaceutically acceptable carriers or diluents.

Compounds useful in the present invention have not been heretofor reported. Thus, the present invention is also directed to novel substituted enaminones having the structure of Formula I. Without being bound by theory proposed herein, it is believed that the compound of Formula I or pharmaceutically acceptable salts thereof act by binding to a site other than a site that binds [$^3$H]-flunitrazepam, barbiturates, loreclezole, [$^3$H]-muscimol or 3α,20α-pregnanediol, thereby altering chloride conductance through the $GABA_A$ receptor complex in a therapeutically usefully fashion.

Further, the present invention is directed to $^3$H, $^{35}$S, $^{36}$Cl, $^{14}$C and $^{125}$I radiolabeled compounds of Formula I and their use as radioligands for their binding site on the GRC.

Additional embodiments and advantages of the invention will be set forth in part in the description that follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIG. 1: Dose response of ethyl 2-chloro-α-[[(4-ethynylphenyl)amino]methylene]-β-oxo-benzenepropionate, α-[[(4-ethynylphenyl)-amino]methylene]-2-chloro-β-oxo-N-propyl-benzenepropanamide, 5α-pregnan-3α-ol-20-one, and clonazepam on 0.2 mM [$^3$H]flunitrazepam binding in rat cortex.

FIG. 2: Dose response of 5α-pregnan-3α, 20α-diol in the absence and presence of 3.0 nM ethyl 2-chloro-α-[[(4-ethynylphenyl)amino]methylene]-β-oxo-benzenepropionate or 100 nM α-[[(4-ethynylphenyl)amino]methylene]-2-chloro-o-oxo-N-propyl-benzenepropanamide on 2 nM [$^{35}$S]TBPS binding in rat cortex.

FIG. 3: Dose response of ethyl 2-chloro-α-[[(4-ethynylphenyl)amino]methylene]-β-oxo-benzenepropionate, α-[[4-ethynylphenyl)amino]methylene]-2-chloro-β-oxo-N-propyl-benzenepropanamide, and γ-aminobutyric acid on 5 nM [$^3$H]muscimol binding in rat cortex.

FIG. 4: Dose response of loreclezole in the presence and absence of 300 nM ethyl 2-chloro-α-[[(4-ethynylphenyl) amino]methylene]-β-oxo-benzenepropionate on 0.2 nM [$^3$H] flunitrazepam binding in rat cortex.

FIG. 5: Dose response of pentobarbital in the presence and absence of 300 nM ethyl 2-chloro-α-[[(4-ethynylphenyl) amino]methylene]-β-oxo-benzenepropionate on 0.2 nM [$^3$H] flunitrazepam binding in rat cortex.

DETAILED DESCRIPTION OF THE INVENTION

In one embodiment, there is provided substituted enaminones represented by Formula I:

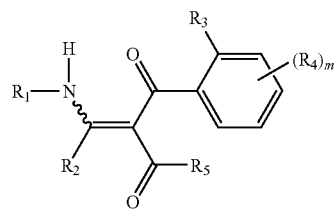

or a pharmaceutically acceptable salt, prodrug or solvate thereof, wherein:

$R_1$ is selected from the group consisting of aryl, heteroaryl, aralkyl and $R_{16}R_{17}N$—, each unsubstituted or substituted;

$R_2$ is selected from the group consisting of hydrogen and unsubstituted or substituted $C_{1-10}$alkyl;

$R_3$ is selected from the group consisting of fluoro, chloro, bromo, iodo, $C_{1-10}$alkoxy, nitro, halo$C_{1-10}$alkyl, perhalo$C_{1-10}$alkyl and unsubstituted or substituted $C_{1-10}$alkyl;

each $R_4$ is independently selected from the group consisting of halogen, nitro, $C_{1-10}$alkyl, $C_{2-10}$-alkenyl, $C_{2-10}$-alkynyl, $C_{1-10}$alkoxy, aralkyl, aryl, heteroaryl, cycloalkyl and heterocycloalkyl, each unsubstituted or substituted, or wherein $R_3$ and an adjacent $R_4$ together form a fused unsubstituted or substituted 5 or 6 membered cycloalkyl, aryl or heteroaryl ring;

$R_5$ is selected from the group consisting of $C_{1-10}$alkyl, $C_{1-10}$alkoxy, —NH$_2$, $C_{1-10}$alkylamino, di($C_{1-10}$)alkylamino and aryl, each unsusbtituted or substituted;

$R_{16}$ and $R_{17}$ are each independently $C_{3-12}$cycloalkyl, aryl, heteroaryl, $C_{1-10}$alkyl, each unsubstituted or substituted, or $R_{16}$ and $R_{17}$ together with the nitrogen atom to which they are attached form an unsusbtituted or substituted 4, 5, or 6 membered ring; and m is 0, 1, 2, 3 or 4; with the proviso that when $R_5$ is -OEt, then $R_4$ is not halogen, and the compound of Formula I is not the compounds ethyl (α-[(benzyl)aminomethylene]-2-chloro-β-oxobenzenepropionate and 1-(2,4-dichloro-5-fluorophenyl)-2-[[(2,4-difluorophenyl) amino]methylene]-1,3-pentanedione.

In another embodiment, there is provided substituted enaminones represented by Formula Ia:

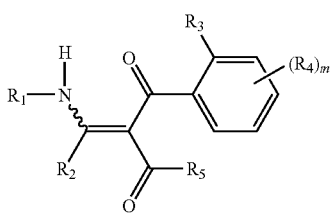

or a pharmaceutically acceptable salt, prodrug or solvate thereof, wherein:

$R_1$ is selected from the group consisting of aryl, heteroaryl, aralkyl and $R_{16}R_{17}N$—, each unsubstituted or substituted;

$R_2$ is selected from the group consisting of hydrogen and unsubstituted or substituted $C_{1-10}$alkyl;

$R_3$ is selected from the group consisting of hydrogen, halo, halo$C_{1-10}$alkyl, perhalo$C_{1-10}$alkyl, amino, cyano, nitro, hydroxy, thio, $C_{1-20}$alkyl, $C_{2-10}$-alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsusbtituted or substituted;

each $R_4$ is independently selected from the group consisting of halogen, nitro, $C_{1-10}$alkyl, $C_{2-10}$alkenyl, $C_{2-10}$alkynyl, $C_{1-10}$alkoxy, aralkyl, aryl, heteroaryl, cycloalkyl and heterocycloalkyl, each unsubstituted or substituted, or wherein $R_3$ and an adjacent $R_4$ together form a fused unsubstituted or substituted 5 or 6 membered cycloalkyl, aryl or heteroaryl ring;

$R_5$ is selected from the group consisting of $C_{1-10}$alkyl, $CH_3O-$, $C_{3-10}$alkoxy, $-NH_2$, $C_{1-10}$alkylamino, di($C_{1-10}$)alkylamino and aryl, each unsubstituted or substituted;

$R_{16}$ and $R_{17}$ are each independently $C_{3-12}$cycloalkyl, aryl, heteroaryl, $C_{1-10}$alkyl, each unsubstituted or substituted, or $R_{16}$ and $R_{17}$ together with the nitrogen atom to which they are attached form an unsusbtituted or substituted 4, 5, or 6 membered ring; and m is 0, 1, 2, 3 or 4. In a particular variation of the above compound of Formula Ia, the compound is the compound wherein $R_5$ is not $CH_3CH_2O-$.

In one aspect, there is provided a compound of the Formula Ib:

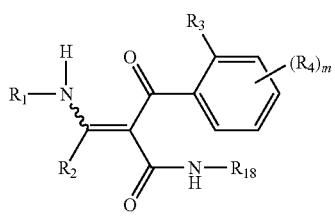

Ib $R_{16}$ and $R_{17}$ are each independently $C_{3-12}$cycloalkyl, aryl, heteroaryl, $C_{1-10}$alkyl, each unsubstituted or substituted, or $R_{16}$ and $R_{17}$ together with the nitrogen atom to which they are attached form an unsusbtituted or substituted 4, 5, or 6 membered ring; and $R_{18}$ is selected from the group consisting of optionally substituted $C_{1-10}$alkyl, arylalkyl, and heterocycloalkyl; and m is 0, 1, 2, 3 or 4.

In another aspect of the compound of the Formula I, when $R_5$ is $C_{1-10}$alkylamino, the stereochemistry of the enaminone is such that the $-NHR_1$ is syn with the $-COR_5$ group as shown in Formula Ib below.

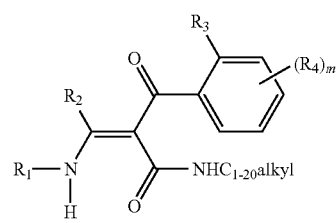

Ib

In another aspect of the compound of Formula Ib, the group $-NHC_{1-20}$alkyl is selected from the group consisting of $-NHC_{2-10}$alkyl. In another aspect, the group $C_{2-10}$-alkyl is iso-propyl, propyl, sec-butyl, tert-butyl, 2-methyl-i-butyl and 3-methyl-1-butyl.

In another aspect, there is provided a compound comprising the Formula Ic:

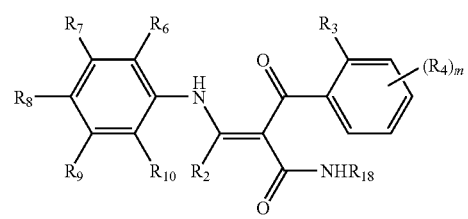

Ic or a pharmaceutically acceptable salt, prodrug or solvate thereof, wherein:

$R_1$ is selected from the group consisting of aryl, heteroaryl, aralkyl and $R_{16}R_{17}N-$, each unsubstituted or substituted;

$R_2$ is selected from the group consisting of hydrogen and unsubstituted or substituted $C_{1-10}$alkyl;

$R_3$ is selected from the group consisting of hydrogen, halo, halo$C_{1-10}$alkyl, perhalo$C_{1-10}$alkyl, amino, cyano, nitro, hydroxy, thio, $C_{1-20}$alkyl, $C_{2-20}$alkenyl, $C_{2-20}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsusbtituted or substituted;

each $R_4$ is independently selected from the group consisting of halo, nitro, halo$C_{1-10}$alkyl, perhalo$C_{1-10}$alkyl, amino, cyano, nitro, hydroxy, thio, $C_{1-20}$alkyl, $C_{2-20}$alkenyl, $C_{2-20}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsusbtituted or substituted, or wherein $R_3$ and an adjacent $R_4$ together form a fused unsubstituted or substituted 5 or 6 membered cycloalkyl, aryl or heteroaryl ring;

or a pharmaceutically acceptable salt, prodrug or solvate thereof, wherein:

$R_2$ is selected from the group consisting of hydrogen, methyl and ethyl;

$R_3$ is selected from the group consisting of hydrogen, halo, halo$C_{1-10}$alkyl, perhalo$C_{1-10}$alkyl, amino, cyano, nitro, hydroxy, thio, $C_{1-20}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsusbtituted or substituted;

each $R_4$ is independently selected from the group consisting of hydrogen, halo, nitro, halo$C_{1-10}$alkyl, perhalo$C_{1-10}$alkyl, amino, cyano, nitro, hydroxy, thio, $C_{1-20}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsusbtituted or substituted, or wherein $R_3$ and an adjacent $R_4$ together form a fused unsubstituted or substituted 5 or 6 membered cycloalkyl, aryl or heteroaryl ring;

$R_6$, $R_7$, $R_8$, $R_9$ and $R_{10}$ are each independently selected from the group consisting of hydrogen, halo, $C_{1-10}$alkyl, $C_{2-10}$alkynyl, $C_{1-10}$alkoxy, aralkyl, cycloalkyl, aryl$C_{1-10}$alkyl and heteroaryl$C_{1-10}$alkyl; or $R_6$ and $R_7$, or $R_7$ and $R_8$, or $R_8$ and R$_9$, or R$_9$ and R$_{10}$ are taken together with the carbon atoms to which they are attached to form an unsubstituted or substituted fused 5 or 6 membered saturated, partially unsaturated ring, aryl or heteroaryl;

R$_{18}$ is selected from the group consisting of C$_{1-10}$alkyl, arylalkyl and heterocycloalkyl, each unsubstituted or substituted; and m is 0, 1, 2, 3 or 4.

In another aspect, there is provided a compound comprising the Formula II:

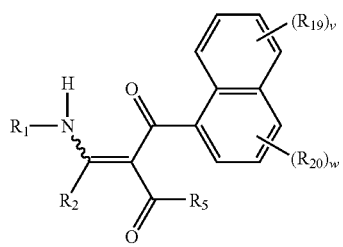

II or a pharmaceutically acceptable salt, prodrug or solvate thereof, wherein:

R$_1$ is selected from the group consisting of aryl, heteroaryl, aralkyl and R$_{16}$R$_{17}$N—, each unsubstituted or substituted;

R$_2$ is selected from the group consisting of hydrogen and unsubstituted or substituted C$_{1-10}$alkyl;

R$_5$ is selected from the group consisting of C$_{1-10}$alkyl, C$_{1-10}$alkoxy, —NH$_2$, C$_{1-10}$alkylamino, di(C$_{1-10}$)alkylamino and aryl, each unsubstituted or substituted;

R$_{16}$ and R$_{17}$ are each independently C$_{3-12}$cycloalkyl, aryl, heteroaryl, C$_{1-10}$alkyl, each unsubstituted or substituted, or R$_{16}$ and R$_{17}$ together with the nitrogen atom to which they are attached form an unsusbtituted or substituted 4, 5, or 6 membered ring;

R$_{19}$ and R$_{20}$ are each independently selected from the group consisting of halo, cyano, nitro, halo(C$_{1-10}$)alkyl, perhalo(C$_{1-5}$)alkyl, aryl, heteroaryl, cycloalkyl, C$_{1-10}$alkyl, aryl (C$_{1-10}$)alkyl, cycloalkyl(C$_{1-10}$)alkyl, hydroxy(C$_{1-10}$)alkyl, amino(C$_{1-10}$)alkyl, alkoxy(C$_{1-10}$)alkyl, amino, hydroxyl, thio, C$_{1-10}$alkoxy and C$_{1-10}$alkylthiol; and v and w are each independently 0, 1, 2 or 3.

In yet another aspect, there is provided a compound comprising the Formula III:

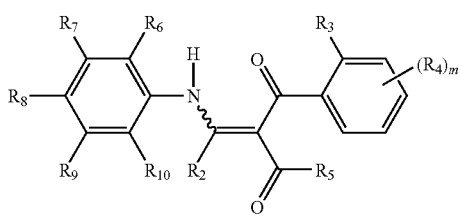

III or a pharmaceutically acceptable salt, prodrug or solvate thereof, wherein:

R$_2$ is selected from the group consisting of hydrogen and unsubstituted or substituted C$_{1-10}$alkyl;

R$_3$ is selected from the group consisting of fluoro, chloro, bromo, iodo, C$_{1-10}$alkoxy, nitro, haloC$_{1-10}$, perhaloC$_{1-10}$and unsubstituted or substituted C$_{1-10}$alkyl;

each R$_4$ is independently selected from the group consisting of halogen, nitro, C$_{1-10}$alkyl, C$_{2-10}$-alkynyl, C$_{1-10}$alkoxy, aralkyl, aryl, heteroaryl, cycloalkyl and heterocycloalkyl, each unsubstituted or substituted, or wherein R$_3$ and an adjacent R$_4$ together form a fused unsubstituted or substituted 5 or 6 membered cycloalkyl, aryl or heteroaryl ring;

R$_5$ is selected from the group consisting of C$_{1-10}$alkyl, C$_{1-10}$alkoxy, -NH$_2$, C$_{1-10}$alkylamino, di(C$_{1-10}$)alkylanino and aryl, each unsubstituted or substituted;

R$_6$, R$_7$, R$_8$, R$_9$ and R$_{10}$ are each independently selected from the group consisting of hydrogen, halo, C$_{1-10}$alkyl, C$_{2-10}$-alkynyl, C$_{1-10}$alkoxy, aralkyl, cycloalkyl, arylC$_{1-10}$alkyl and heteroarylC$_{1-10}$alkyl; or R$_6$ and R$_7$, or R$_7$ and R$_8$, or R$_8$ and R$_9$, or R$_9$ and R$_{10}$ are taken together with the carbon atoms to which they are attached to form an unsubstituted or substituted- fused 5 or 6 membered saturated, partially unsaturated ring, aryl or heteroaryl;

and m is 0, 1, 2, 3 or 4.

In another aspect, there is provided a compound comprising the Formula IV:

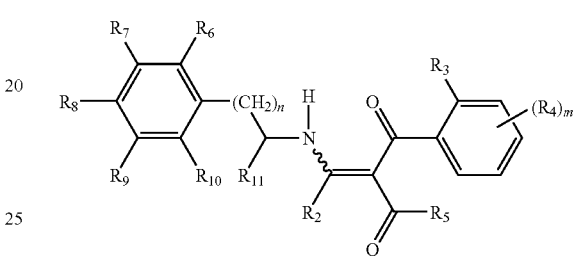

IV or a pharmaceutically acceptable salt, prodrug or solvate thereof, wherein:

R$_2$ is selected from the group consisting of hydrogen and unsubstituted or substituted C$_{1-10}$alkyl;

R$_3$ is selected from the group consisting of fluoro, chloro, bromo, iodo, C$_{1-10}$alkoxy, nitro, haloC$_{1-10}$, perhaloC$_{1-10}$alkyl and unsubstituted or substituted C$_{1-10}$alkyl;

each R$_4$ is independently selected from the group consisting of halogen, nitro, C$_{1-10}$alkyl, C$_{2-10}$-alkynyl, C$_{1-10}$alkoxy, aralkyl, aryl, heteroaryl, cycloalkyl and heterocycloalkyl, each unsubstituted or substituted, or wherein R$_3$ and an adjacent R$_4$ together form a fused unsubstituted or substituted 5 or 6 membered cycloalkyl, aryl or heteroaryl ring;

R$_5$ is selected from the group consisting of C$_{1-10}$alkyl, C$_{1-10}$alkoxy, -NH$_2$, C$_{1-10}$alkylamino, di(C$_{1-10}$)alkylamino and aryl, each unsubstituted or substituted;

R$_6$, R$_7$, R$_8$, R$_9$ and R$_{10}$ are each independently selected from the group consisting of hydrogen, halo, C$_{1-10}$alkyl, C$_{2-10}$alkynyl, C$_{1-10}$alkoxy, aralkyl, cycloalkyl, arylC$_{1-10}$alkyl and heteroarylC$_{1-10}$alkyl; or R$_6$ and R$_7$, or R$_7$ and R$_8$, or R$_8$ and R$_9$, or R$_9$ and R$_{10}$ are taken together with the carbon atoms to which they are attached to form an unsubstituted or substituted fused 5 or 6 membered saturated, partially unsaturated ring, aryl or heteroaryl;

R$_{11}$ is hydrogen or is an unsubstituted or substituted C$_{1-10}$alkyl; m is 0, 1, 2, 3 or 4; and n is 0, 1, 2, 3, 4 or 5.

In yet another aspect, there is provided a comprising the Formula IVa:

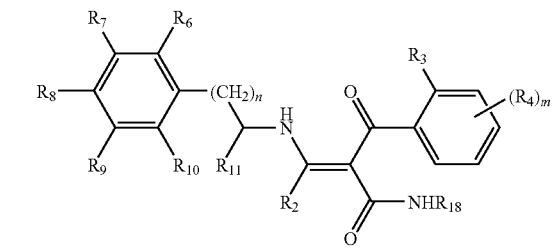

or a pharmaceutically acceptable salt, prodrug or solvate thereof, wherein:

$R_2$ is selected from the group consisting of hydrogen, methyl and ethyl;

$R_3$ is selected from the group consisting of hydrogen, halo, haloC$_{1-10}$, perhaloC$_{1-10}$, amino, cyano, nitro, hydroxy, thio, C$_{1-20}$alkyl, C$_{1-10}$-alkenyl, C$_{1-10}$-alkynyl, cycloalkyl, heterocycloalkyl, aryl, aralkyl, heteroaryl, C$_{1-10}$alkoxy, aryloxy, heteroaryloxy, carbonyl group, sulfonyl group, sulfinyl group, imino group, each unsusbtituted or substituted; each $R_4$ is independently selected from the group consisting of halogen, nitro, C$_{1-10}$alkyl, C$_{2-10}$-alkynyl, C$_{1-10}$alkoxy, aralkyl, aryl, heteroaryl, cycloalkyl and heterocycloalkyl, each unsubstituted or substituted, or wherein $R_3$ and an adjacent $R_4$ together form a fused unsubstituted or substituted 5 or 6 membered cycloalkyl, aryl or heteroaryl ring;

$R_5$ is selected from the group consisting of C$_{1-10}$alkyl, C$_{1-10}$alkoxy, -NH$_2$, C$_{1-10}$alkylamino, di(C$_{1-10}$)alkylamino and aryl, each unsubstituted or substituted;

$R_6$, $R_7$, $R_8$, $R_9$ and $R_{10}$ are each independently selected from the group consisting of hydrogen, halo, C$_{1-10}$alkyl, C$_{2-10}$-alkynyl, C$_{1-10}$-alkoxy, aralkyl, cycloalkyl, arylC$_{1-10}$alkyl and heteroarylC$_{1-10}$alkyl; or $R_6$ and $R_7$, or $R_7$ and $R_7$, or $R_8$ and $R_9$, or $R_9$ and $R_{10}$ are taken together with the carbon atoms to which they are attached to form an unsubstituted or substituted fused 5 or 6 membered saturated, partially unsaturated ring, aryl or heteroaryl;

$R_{11}$ is hydrogen or is an unsubstituted or substituted C$_{1-10}$alkyl;

$R_{18}$ is selected from the group consisting of C$_{1-10}$alkyl, arylalkyl and heterocycloalkyl, each unsubstituted or substituted; and m is 0, 1, 2, 3 or 4; and n is 0, 1, 2, 3, 4 or 5.

In another aspect, there is provided a compound comprising the Formula V:

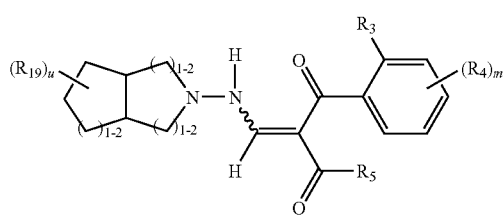

or a pharmaceutically acceptable salt, prodrug or solvate thereof, wherein:

$R_3$ is selected from the group consisting of hydrogen, halo, haloC$_{1-10}$, perhaloC$_{1-10}$, amino, cyano, nitro, hydroxy, thio, C$_{1-20}$alkyl, C$_{2-10}$-alkenyl, C$_{2-10}$-alkynyl, cycloalkyl, heterocycloalkyl, aryl, aralkyl, heteroaryl, C$_{1-10}$alkoxy, aryloxy, heteroaryloxy, carbonyl group, sulfonyl group, sulfinyl group, imino group, each unsusbtituted or substituted;

each $R_4$ is independently selected from the group consisting of hydrogen, halo, haloC$_{1-10}$, perhaloC$_{1-10}$, amino, cyano, nitro, hydroxy, thio, C$_{1-20}$alkyl, C$_{2-10}$-alkenyl, C$_{2-10}$-alkynyl, cycloalkyl, heterocycloalkyl, aryl, aralkyl, heteroaryl, C$_{1-10}$alkoxy, aryloxy, heteroaryloxy, carbonyl group, sulfonyl group, sulfinyl group, imino group, each unsusbtituted or substituted, or wherein $R_3$ and an adjacent $R_4$ together form a fused unsubstituted or substituted 5 or 6 membered cycloalkyl, aryl or heteroaryl ring;

$R_5$ is selected from the group consisting of alkyl, alkoxy, amino, alkylamino, dialkylamino and aryl, each unsubstituted or substituted;

each $R_{19}$ is independently selected from the group consisting of halogen, C$_{1-10}$alkyl, C$_{2-10}$-alkynyl, C$_{1-10}$alkoxy, aralkyl and cycloalkyl, each unsubstituted or substituted; m is 0, 1, 2, 3 or 4; and u is 0, 1 or 2.

In yet another aspect, there is provided a compound comprising the Formula Va:

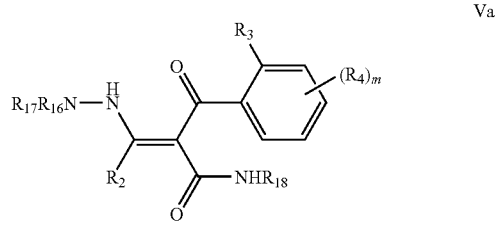

or a pharmaceutically acceptable salt, prodrug or solvate thereof, wherein:

$R_2$ is selected from the group consisting of hydrogen and unsubstituted or substituted C$_{1-10}$alkyl;

$R_3$ is selected from the group consisting of hydrogen, halo, haloC$_{1-10}$, perhaloC$_{1-10}$, amino, cyano, nitro, hydroxy, thio, C$_{1-20}$alkyl, C$_{2-10}$-alkenyl, C$_{2-10}$-alkynyl, cycloalkyl, heterocycloalkyl, aryl, aralkyl, heteroaryl, C$_{1-10}$alkoxy, aryloxy, heteroaryloxy, carbonyl group, sulfonyl group, sulfinyl group, imino group, each unsusbtituted or substituted;

each $R_4$ is independently selected from the group consisting of hydrogen, halo, haloC$_{1-10}$, perhaloC$_{1-10}$, amino, cyano, nitro, hydroxy, thio, C$_{1-20}$alkyl, C$_{2-10}$alkenyl, C$_{2-20}$alkynyl, cycloalkyl, heterocycloalkyl, aryl, aralkyl, heteroaryl, C$_{1-10}$alkoxy, aryloxy, heteroaryloxy, carbonyl group, sulfonyl group, sulfinyl group, imino group, each unsusbtituted or substituted, or wherein $R_3$ and an adjacent $R_4$ together form a fused unsubstituted or substituted 5 or 6 membered cycloalkyl, aryl or heteroaryl ring;

$R_{16}$ and $R_{17}$ are each independently C$_{3-12}$cycloalkyl, aryl, heteroaryl, C$_{1-10}$alkyl, each unsubstituted or substituted, or $R_{16}$ and $R_{17}$ together with the nitrogen atom to which they are attached form an unsusbtituted or substituted 4, 5, or 6 membered ring;

$R_{18}$ is selected from the group consisting of C$_{1-10}$alkyl, arylalkyl, and heterocycloalkyl, each unsubstituted or substituted; and m is 0, 1, 2, 3 or 4.

In yet another aspect, there is provided a compound comprising the Formula VI:

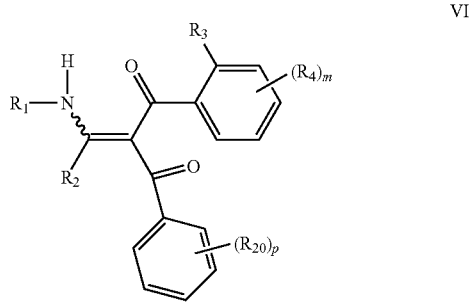

or a pharmaceutically acceptable salt, prodrug or solvate thereof, wherein:

$R_1$ is selected from the group consisting of aryl, heteroaryl, aralkyl and $R_{16}R_{17}N$—, each unsubstituted or substituted;

$R_2$ is selected from the group consisting of hydrogen and unsubstituted or substituted $C_{1-10}$alkyl;

$R_3$ is selected from the group consisting of hydrogen, halo, halo$C_{1-10}$, perhalo$C_{1-10}$alkyl, amino, cyano, nitro, hydroxy, thio, $C_{1-20}$alkyl, $C_{2-10}$-alkenyl, $C_{2-10}$-alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsusbtituted or substituted;

each $R_4$ is independently selected from the group consisting of halogen, nitro, $C_{1-10}$-alkyl, $C_{2-10}$alkynyl, $C_{1-10}$alkoxy, aralkyl, aryl, heteroaryl, cycloalkyl and heterocycloalkyl, each unsubstituted or substituted, or wherein $R_3$ and an adjacent $R_4$ together form a fused unsubstituted or substituted 5 or 6 membered cycloalkyl, aryl or heteroaryl ring;

$R_{16}$ and $R_{17}$ are each independently $C_{3-12}$cycloalkyl, aryl, heteroaryl, $C_{1-10}$alkyl, each unsubstituted or substituted, or $R_{16}$ and $R_{17}$ together with the nitrogen atom to which they are attached form an unsusbtituted or substituted 4, 5, or 6 membered ring; and each $R_{20}$ is independently selected from the group consisting of halo, cyano, nitro, halo($C_{1-10}$)alkyl, perhalo($C_{1-5}$)alkyl, aryl, heteroaryl, $C_{1-10}$alkyl, aryl($C_{1-10}$)alkyl, alkoxy($C_{1-10}$)alkyl, amino, hydroxyl, thio and $C_{1-10}$alkoxy, and m and p are each independently 0, 1, 2, 3 or 4.

In one variation of the above compound, $R_8$ is selected from the group consisting of $C_{1-10}$alkyl, halogen, and $C_{1-10}$alkoxy; and $R_6$, $R_7$, $R_9$ and $R_{10}$ are hydrogen. In another variation of the above compound, $R_3$ is selected from the group consisting of methyl, trifluoromethyl and chloro; and m is 0.

In one embodiment, there is provided a pharmaceutical composition, comprising the compound of Formula I:

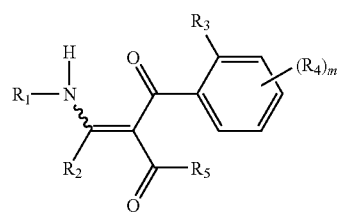

or a pharmaceutically acceptable salt, prodrug or solvate thereof, wherein:

$R_1$ is selected from the group consisting of aryl, heteroaryl, aralkyl and $R_{16}R_{17}N$—, each unsubstituted or substituted;

$R_2$ is selected from the group consisting of hydrogen and unsubstituted or substituted $C_{1-10}$alkyl;

$R_3$ is selected from the group consisting of fluoro, chloro, bromo, iodo, $C_{1-10}$alkoxy, nitro, halo$C_{1-10}$, perhalo$C_{1-10}$ and unsubstituted or substituted $C_{1-10}$alkyl;

each $R_4$ is independently selected from the group consisting of halogen, nitro, $C_{1-10}$alkyl, $C_{2-10}$-alkenyl, $C_{2-10}$-alkynyl, $C_{1-10}$alkoxy, aralkyl, aryl, heteroaryl, cycloalkyl and heterocycloalkyl, each unsubstituted or substituted, or wherein $R_3$ and an adjacent $R_4$ together form a fused unsubstituted or substituted 5 or 6 membered cycloalkyl, aryl or heteroaryl ring;

$R_5$ is selected from the group consisting of optionally substituted $C_{1-10}$alkyl, $C_{1-10}$alkoxy, -NH$_2$, $C_{1-10}$alkylamino, di($C_{1-10}$)alkylamino and aryl;

$R_{16}$ and $R_{17}$ are each independently $C_{3-12}$cycloalkyl, aryl, heteroaryl, $C_{1-10}$alkyl, each unsubstituted or substituted, or $R_{16}$ and $R_{17}$ together with the nitrogen atom to which they are attached form an unsusbtituted or substituted 4, 5, or 6 membered ring; and m is 0, 1, 2, 3 or 4; with the proviso that when $R_5$ is -OEt, then $R_4$ is not halogen, and the compound of Formula I is not the compounds ethyl α-[(benzyl)aminomethylene]-2-chloro-β-oxobenzenepropionate and 1-(2,4-dichloro-5-fluorophenyl)-2-[[(2,4-difluorophenyl)amino]methylene]-1,3-pentanedione; and a pharmaceutically-acceptable carrier selected from the group consisting of excipients and auxiliaries.

Also provided herein are the above compounds wherein the compounds are present as a single stereoisomer and mixtures of stereoisomers and their pharmaceutically acceptable salts. In addition, there is provided the pharmaceutical compositions of the above compounds wherein the composition is formulated for oral administration, parentaral, intraavenous, transdermal, sublingual, intramuscular, rectal, intranasal, intraoccular or subcutaneous administration.

In yet another aspect, there is provided a pharmaceutical composition comprising each of the above compound and a pharmaceutically-acceptable carrier selected from the group consisting of excipients and auxiliaries.

In another aspect, there is provided a method for the treatment of CNS disorders amenable to modulation of the GABA$_A$ receptor complex which comprises administering to a patient in need of such treatment a compound of Formula I:

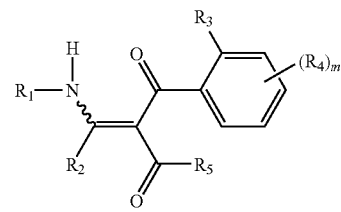

or a pharmaceutically acceptable salt, prodrug or solvate thereof, wherein each of the variables are as defined above. In one variation of the above method, the CNS disorder is an anxiety disorder. In another variation, the CNS disorder is convulsions. In another variation, the CNS disorder is insomnia. In yet another variation, the CNS disorder is a major depressive or bipolar disorder. In yet another variation, the CNS disorder is chronic or acute pain. In another variation, the CNS disorder is a neuroses. In a particular variation, the CNS disorder is withdrawal-induced convulsions from substance abuse. In yet another particular variation, the CNS disorder is a phobia. In another variation of the above method, the CNS disorder is a panic disorder.

In one variation of the above method, the CNS disorder is a generalized anxiety disorder. In another variation, the CNS disorder is an obsessive-compulsive disorder. In yet another variation, the CNS disorder is a post traumatic and acute stress disorder. In another variation, the CNS disorder is a migraine. In one particular variation of the method, the CNS disorder is a bipolar manic disorder; or a cognition deficit disorder. In a particular variation of the above method, the CNS disorder is selected from the group consisting of anxiety and stress related disorders, depression and other affective disorders, epilepsy and other seizure disorders, insomnia and related sleep disorders, acute and chronic pain and cough.

In another aspect, there is provided a method for the treatment of disorders related to learning and memory comprising the steps of administering to a patient in need of such a treatment a compound of the Formula I above. In one variation of the method, the disorder relating to learning and memory is selected from the group consisting of mild cognitive impairment, age related cognitive decline, senile dementia, Alzheimer's disease, sleep disorders involving reduced wakefulness. In another variation, the sleep disorder involving reduced wakefulness is selected from the group consisting of narcolepsy and idiopathic hypersornia. In yet another variation, there is provided a method wherein the compound of Formula I or a pharmaceutically acceptable salt thereof acts by binding to a site other than a site that binds [$^3$H]-flunitrazepam, barbiturates, loreclezole, [$^3$H]-muscimol or 3α,20α-pregnanediol, thereby altering chloride conductance through the GABA$_A$ receptor complex in a therapeutically usefully fashion. In yet another aspect, there is provided a method for the treatment of CNS disorders amenable to modulation of the GABA$_A$ receptor complex which comprises administering to a patient in need of such treatment a compound of Formula I.

α7 Nicotinic Acetylcholine Receptor Modulators:

The present invention is also related to the discovery that certain substituted enaminones represented by Formulae I-VI act as novel modulators of α7 nicotinic acetylcholine receptors (nAChRs). The invention is related with treating disorders responsive to enhancement of acetylcholine action on α7 nAChRs in a mammal by administering an effective amount of a compound of Formulae I-VI as described herein. The compounds of the present invention, being ligands for α7 nAChRs, are therefore of use in the treatment and/or prevention of a variety of disorders of the central nervous system. Such disorders include neurodegenerative diseases, senile dementias and schizophrenia. Another aspect of the present invention is directed to the use of the compounds of Formulae I-VI as enhancers of acetylcholine-facilitated monovalent and divalent cation flux mediated through the α7 nAChR. Also, an aspect of the present invention is to provide a pharmaceutical composition useful for treating disorders responsive to the enhancement of acetylcholine-facilitated monvalent and divalent cation mediated flux through the nAChR, containing an effective amount of a compound of Formulae I-VI in a mixture with one or more pharmaceutically acceptable carriers or diluents.

In one aspect, there is provided a method for the treatment of CNS disorders amenable to modulation of the nAChR complex which comprises administering to a patient in need of such treatment a compound of Formula I:

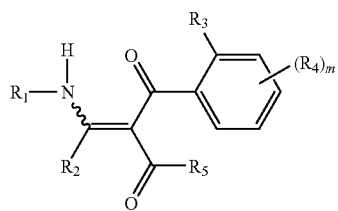

I or a pharmaceutically acceptable salt, prodrug or solvate thereof, wherein:

$R_1$ is selected from the group consisting of aryl, heteroaryl, aralkyl and $R_{16}R_{17}N$—, each unsubstituted or substituted;

$R_2$ is selected from the group consisting of hydrogen and unsubstituted or substituted $C_{1-10}$alkyl;

$R_3$ is selected from the group consisting of hydrogen, halo, halo$C_{1-10}$, perhalo$C_{1-10}$, amino, cyano, nitro, hydroxy, thio, $C_{1-20}$alkyl, $C_{2-10}$-alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsusbtituted or substituted;

each $R_4$ is independently selected from the group consisting of hydrogen, halo, halo$C_{2-10}$alkyl, perhalo$C_{1-10}$ alkyl, amino, cyano, nitro, hydroxy, thio, $C_{1-20}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsusbtituted or substituted, or wherein $R_3$ and an adjacent $R_4$ together form a fused unsubstituted or substituted 5 or 6 membered cycloalkyl, aryl or heteroaryl ring;

$R_5$ is selected from the group consisting of optionally substituted $C_{1-10}$alkyl, $C_{1-10}$alkoxy, -NH$_2$, $C_{1-10}$alkylamino, di($C_{1-10}$)alkylamino and aryl;

$R_{16}$ and $R_{17}$ are each independently $C_{3-12}$cycloalkyl, aryl, heteroaryl, $C_{1-10}$alkyl, each unsubstituted or substituted, or $R_{16}$ and $R_{17}$ together with the nitrogen atom to which they are attached form an unsusbtituted or substituted 4, 5, or 6 membered ring; and m is 0, 1, 2, 3 or 4.

In another aspect, there is provided a method for the treatment of neurodegenerative disorders, which comprises administering to a patient in need of such treatment an effective amount of compound of the Formulae I-VI. In yet another aspect, there is provided a method for the treatment of senile dementias, which comprises administering to a patient in need of such treatment an effective amount of compound of the Formulae I-VI. In another aspect, there is provided a method for the treatment of schizophrenia, which comprises administering to a patient in need of such treatment an effective amount of compound of the Formulae I-VI. In yet another aspect, there is provided a method for the treatment of cognition deficit disorders, which comprises administering to a patient in need of such treatment an effective amount of compound of the Formulae I-VI. In another aspect, there is provided a method for the treatment of disorders related to learning and memory such as mild cognitive impairment, age related cognitive decline, senile dementia, Alzheimer's disease, by inhibition of mono and divalent cation conductance through the site mediating the action of compound of the above Formulae I-VI.

Compounds of Formulae I-VI include:

Ethyl 2-chloro-β-oxo-α-[[[4-(1,2,3,4-tetrahydronaphthyl-1-amino)phenyl]amino]-methylene]benzenepropionate;

Ethyl 2-chloro-5-nitro-β-oxo-α-[[[4-(1,2,3,4-tetrahydronaphthyl-1-amino)-phenyl]amino]methylene]benzenepropionate;

Ethyl 2-chloro-α-[(cyclohexylamino)methylene]-o-oxobenzenepropionate;

Ethyl 2-chloro-α-[(4-iodophenyl)aminomethylene]-β-oxo-benzenepropionate;

Ethyl α-[(4-bromophenyl)aminomethylene]-2-chloro-o-oxo-benzenepropionate;

Ethyl 2-chloro-α-[(4-methoxyphenyl)aminomethylene]-β-oxo-benzene-propionate;

Ethyl 2-chloro-α-[(3-chloro-4-fluorophenyl)aminomethylene]-β-oxo-benzene-propionate;

Ethyl 2-chloro-α-[(4-fluorophenyl)aminomethylene]-β-oxo-benzenepropionate;

Ethyl α-[(4-iodophenyl)aminomethylene]-β-oxo-1-naphthalene propionate;

Ethyl α-[(4-fluorophenyl)aminomethylene]-β-oxo-1-naphthalene propionate;

Ethyl α-[(benzyl)aminomethylene]-β-oxo-1-naphthalenepropionate;
Ethyl β-oxo-α-[(2-phenylethyl)aminomethylene]-1-naphthalenepropionate;
Ethyl β-oxo-α-[(3-phenylpropyl)aminomethylene]-1-naphthalenepropionate;
Ethyl β-oxo-α-[(4-phenylbutyl)aminomethylene]-1-naphthalenepropionate;
Ethyl 2-chloro-α-[(3-phenylpropyl)aminomethylene]-β-oxo-benzenepropionate;
Ethyl 2-chloro-α-[(3,3-diphenylpropyl)aminomethylene]-β-oxo-benzenepropionate;
Ethyl 2-chloro-β-oxo-α-[(4-phenylbutyl)aminomethylene]-benzenepropionate;
Ethyl 2-bromo-α-[(4-fluorophenyl)aminomethylene]-β-oxo-benzenepropionate;
Ethyl α-[(4-fluorophenyl)aminomethylene]-2-nitro-o-oxo-benzenepropionate;
Ethyl α-[(4-fluorophenyl)aminomethylene]-2-methyl-β-oxo-benzenepropionate;
Ethyl 2-methyl-β-oxo-α-[(4-phenylbutyl)aminomethylene]-benzenepropionate;
Ethyl 2-nitro-β-oxo-α-[(4-phenylbutyl)aminomethylene]-benzenepropionate;
Ethyl 2-ethoxy-β-oxo-α-[(4-phenylbutyl)aminomethylene]-benzenepropionate;
Methyl 2-chloro-α-[(4-iodophenyl)aminomethylene]-β-oxo-benzenepropionate;
Ethyl α-[(4-iodophenyl)aminomethylene]-β-oxo-2-trifluoromethyl-benzenepropionate;
Ethyl α-[(4-iodophenyl)aminomethylene]-2-methyl-β-oxo-benzenepropionate;
Ethyl α-[(4-methoxyphenyl)aminomethylene]-β-oxo-2-trifluoromethyl-benzenepropionate;
Ethyl 2-bromo-α-[(4-iodophenyl)aminomethylene]-β-oxo-benzenepropionate;
Ethyl 2-chloro-α-[(4-methylphenyl)aminomethylene]-β-oxo-benzenepropionate;
Ethyl α-[(4-butylphenyl)aminomethylene]-2-chloro-β-oxo-benzenepropionate;
Ethyl 2-chloro-α-[(4-isopropylphenyl)aminomethylene]-β-oxo-benzene-propionate;
Ethyl 2-bromo-α-[(4-iodophenyl)aminomethylene]-β-oxo-benzenepropionate;
2-Chloro-α-[[(4-cyanophenyl)amino]methylene]-N-ethyl-β-oxo-benzenepropanamide;
2-Chloro-N-ethyl-c:-[[(4-iodophenyl)amino]methylene]-β-oxo-benzenepropanamide;
2-Chloro-α-[[(4-iodophenyl)amino]methylene]-β-oxo-N-(2-propynyl)-benzenepropanamide;
2-Chloro-α-[[(4-ethynylphenyl)amino]methylene]-β-oxo-N-propyl-benzenepropanamide;
α-[[(4-Ethynylphenyl)amino]methylene] -2-methyl-β-oxo-N-propyl-benzenepropanamide;
α-[[(4-Cyanophenyl)amino]methylene]-2-methyl-β-oxo-N-propyl-benzenepropanamide;
α-[[(4-Ethynylphenyl)amino]methylene]-2-methyl-β-oxo-N-(2-propynyl)-benzenepropanamide;
2-Chloro-α-[[(4-cyanophenyl)amino]methylene]-β-oxo-N-propyl-benzenepropanamide;
Ethyl α-[(4-iodophenyl)aminomethylene]-2-methyl-β-oxo-benzenepropionate;
2-Chloro-N-ethyl-α-[(isoxazolyl-3-amino)methylene]-β-oxo-benzenepropanamide;
α-[(4-Ethynylphenyl)aminomethylene]-β-oxo-N-propyl-1-naphthalenepropanamide;
2-Chloro-α-[(isoxazolyl-3-amino)methylene]-β-oxo-N-propyl-benzenepropanamide;
2-Chloro-N-ethyl-β-oxo-α-[(1,2,4-triazolyl-4-amino)methylene]benzene-propanamide;
Ethyl α-[(4-ethynylphenyl)aminomethylene]-2-fluoro-β-oxobenzenepropionate;
α-[(4-Ethynylphenyl)aminomethylene]-β-oxo-N-propyl-1-naphthalenepropanamide; and
2-Chloro-N-ethyl-β-oxo-α-[(pyrazinyl)amino]-benzenepropanamide.

For use in medicine, the salts of the compounds of Formulae I-VI will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, fumaric acid, maleic acid, succinic acid, acetic acid, benzoic acid, oxalic acid, citric acid, tartaric acid, or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Standard methods for the preparation of pharmaceutically acceptable salts and their formulations are well known in the art, and are disclosed in various references, including for example, "Remington: The Science and Practice of Pharmacy", A. Gennaro, ed., 20$^{th}$ edition, Lippincott, Williams & Wilkins, Philadelphia, Pa.

The present invention includes within its scope prodrugs of the compounds of Formulae I-VI above. In general, such prodrugs will be functional derivatives of the compounds of Formulae I-VI that are readily convertible in vivo into the required compound of Formulae I-VI. Conventional procedures for the selection and preparation of suitable prodrug derivatives are described, for example, in Design of Prodrugs, ed. H. Bundgaard, Elsevier, 1985.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention.

"Disease" means any unhealthy condition of an animal or any unhealthy condition of an animal that may be caused by medical therapy to the animal from a therapy. Example of a disease caused by therapy include, for example, therapies that may result in one or more side effects.

"Halogen" or "halo" means fluorine, bromine, chlorine and iodine. Useful halogens include fluorine, chlorine, bromine and iodine.

"Alkyl" means a straight or branched, saturated or unsaturated aliphatic radical with the number of carbon atoms depicted. An alkyl group may comprise a heteroatom, such as an oxygen, nitrogen or sulfur inserted within or in the chain of the alkyl group. Useful alkyl groups include straight chain and branched $C_{1-20}$alkyl groups. In one aspect, the alkyl group of the present invention comprises the $C_{5-20}$alkyl groups. Typical $C_{5-20}$alkyl groups include n-penyl, n-hexyl, n-heptyl, n-octyl, n-nonyl, n-decyl, n-undecyl, n-dodecyl, n-tricedyl, n-tetradecyl, n-pentadecyl, n-hexadecyl, n-heptadecyl, n-octadecyl, n-nonadecyl and eicosanyl groups. An alkyl group may also be represented with another group, such as an "arylalkyl" group, such as a benzyl group. See below.

An "aryl" group may be a monocyclic, bicyclic or polycyclic ring system wherein each ring is aromatic, or when fused or connected to one or more rings to form a polycyclic ring system. An aryl ring may also be fused with a non-aromatic ring. An aryl ring may also contain a heteroatom to form a hetroaryl ring. Useful aryl groups are $C_{6-14}$aryl, especially $C_{6-10}$aryl. Typical $C_{6-14}$aryl groups include phenyl, naphthyl, anthracyl, indenyl and biphenyl groups.

An "arylalkyl" or "aralkyl" group includes any of the above-mentioned $C_{1-20}$alkyl groups substituted with any of the above-mentioned $C_{6-10}$aryl groups. Similarly, a substituted $C_{1-10}$alkyl may also represent an arylalkyl or aralkyl group (or heteroarylalkyl, etc . . . ) when the $C_{1-10}$alkyl group is substituted with an aryl group. Useful arylalkyl groups include benzyl, phenethyl and phenylpropyl. When a combination group such as a arylalkyl or aralkyl group is represented, the group is attached at the latter or last represented group. For example, an "aryl$C_{1-10}$alkyl" group, such as a benzyl group, for example, is attached at the bond represented here as aryl$C_{1-10}$alkyl- or benzyl-.

Useful cycloalkylalkyl groups include any of the above-mentioned $C_{1-10}$alkyl groups substituted with any of the previously mentioned cycloalkyl groups. A cycloalkyl group may also comprise one or more heteroatoms in the cyclic group. Examples of useful cycloalkylalkyl groups include cyclohexylmethyl and cyclopropylmethyl groups.

Useful halomethyl groups include $C_{1-10}$alkyl groups substituted with one or more fluorine, chlorine, bromine or iodine atoms, including fluoromethyl, difluoromethyl, trifluoromethyl and 1,1-difluoroethyl groups. Perhaloalkyl group include, for example, trifluoromethyl and pentafluoroethyl groups.

Useful hydroxyalkyl groups include $C_{1-20}$alkyl groups substituted by hydroxy group, including hydroxymethyl, 1- and 2-hydroxyethyl and 1-hydroxypropyl groups.

Useful alkoxy groups include oxygen substitution by one of the $C_{1-20}$alkyl groups described above. Examples of such alkoxy groups include methoxy, ethoxy, propoxy, butoxy, and the like.

Useful alkylthio groups include sulfur substitution by one of the $C_{1-20}$alkyl groups described above, including for example, thiomethyl, thiobutyl, decyl- and hexadecylthio groups.

An "amino" group is —$NH_2$. An alkylamino and dialkylamino groups, for example, include the groups —$NHR_{12}$ and -$NR_{12}R_{13}$, wherein each $R_{12}$ and $R_{13}$ are independently substituted or unsubstituted $C_{1-20}$alkyl groups. Example of such groups include —NHMe, —NHEt, —NHcyclohexyl, —NHCH$_2$phenyl, —N(Me)$_2$, and the like. Useful dialkylaminoalkyl groups include any of the above-mentioned $C_{1-10}$alkyl groups, each substituted or unsubstituted. Also, a substituted amino group may include for example, —NHMe, —NHEt, —NHcyclohexyl, —N(Me)$_2$ and the like, and —NHCOMe, —NHCOEt, —NHCONHMe, and the like.

"Imino" means the group —C(=N)— that may be attached to another ligand such as an -$NR_aR_b$ or an —$OR_a$ group, for example, to form a —C(=N)$NR_aR_b$ or a —C(=N)$OR_a$, respectively.

Useful alkylthiol groups include any of the above-mentioned $C_{1-10}$alkyl groups substituted by a —SH group.

"Carbonyl" means the group —C(O)— that may be attached to another ligand such as an —$NR_aR_b$ or an —$OR_a$ group, for example, to form a —C(O)$NR_aR_b$ or a —C(O)$OR_a$, respectively. Additional examples of carbonyl groups include a carboxy group, aldehyde, acid halide or ketone. A carboxy or carboxyl group is —COOH.

"Heterocyclic" means a saturated or partially unsaturated 3-7 membered monocyclic or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or nitrogen if the resulting compound is stable. Examples include, but are not limited to pyrrolidine, piperidine, piperazine, morpholine, quinoline, 1,2,3,4-tetrahydroquinoline, and the like.

"Heteroaryl" means wholly unsaturated 5 and 6 membered monocyclic, or 9 and 10 membered bicyclic ring system for example, which consists of carbon atoms and from one to four heteroatoms independently selected from the group consisting of O, N and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or nitrogen if the resulting compound is stable. Examples include, but are not limited to thiophene, benzothiophene, imidazole, pyridine, pyrimidine, quinoline, naphthyridine, purine and the like. The heteroaryl groups may be unsubstituted or substituted.

"Substituted or unsubstituted" means that a group may consist of only hydrogen substituents (unsubstituted) or may further comprise one or more non-hydrogen substituents (substituted) that are not otherwise specified. For example, tert-butyl group may be an example of a propyl group that is substituted by a methyl group. Examples of substituents include, but are not limited to, ($C_{1-10}$)alkyl, ($C_{2-10}$)alkylene, amide, amino, aryl, carbamoyl, carbonyl group, cycloalkyl, ester, halo, heteroaryl, oxo, hydroxy or nitro groups, each of which may also be substituted or unsubstituted as valency permits. Optional substituents on $R_1$ to $R_{20}$ include any one or more of halo, cyano, nitro, halo($C_{1-20}$)alkyl, perhalo($C_{1-20}$) alkyl, aryl, cycloalkyl, $C_{1-20}$alkyl, aryl($C_{1-20}$)alkyl, cycloalkyl($C_{1-20}$)alkyl, hydroxy($C_{1-20}$)alkyl, amino($C_{1-20}$) alkyl, alkoxy($C_{1-20}$)alkyl, amino, hydroxy, thiol, alkoxy and $C_{1-20}$alkylthiol groups mentioned above. In one aspect, a preferred optional substituents include halo, ($C_{1-6}$)alkyl, halo ($C_{1-6}$)alkyl, amino($C_{1-6}$)alkyl, $C_{1-20}$alkoxy and amino.

"Isomers" mean any compound with an identical molecular formula but having a difference in the nature or sequence of bonding or arrangement of the atoms in space. Examples of such isomers include, for example, E and Z isomers of double bonds, enantiomers, and diastereomers. Compounds of the present invention depicting a bond with a "squiggly line" representation is intended to encompass a single isomer and/ or both isomers of the double bond as shown below.

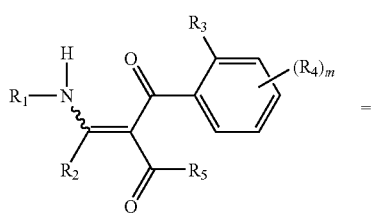

-continued

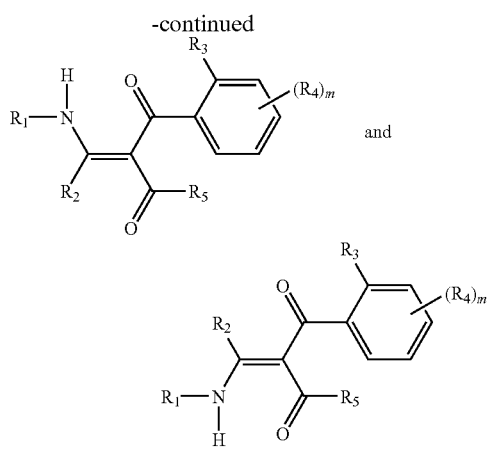

and

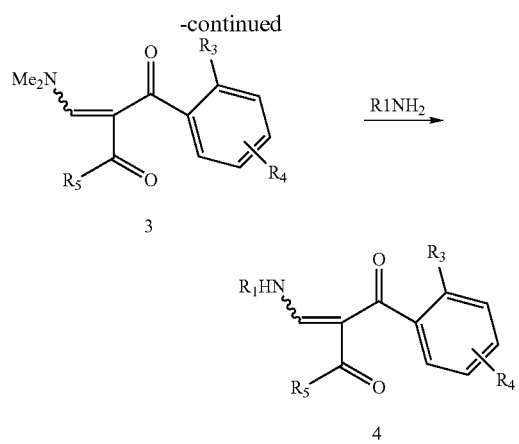

"Prodrug" means a compound that may be converted in vivo metabolically into a compound of the present invention. For example, the prodrug of a compound of the present invention may or may not have biological activity as an agonist. Examples of prodrugs are known in the art. Examples of prodrugs are provided in T. Higuchi and V. Stella, Pro-drugs as Novel Delivery Systems, Vol. 14 of the *A.C.S. Symposium Series;* and in Edward B. Roche, ed., *Bioreversible Carriers in Drug Design*, American Pharmaceutical Association and Pergamon Press, 1987, both references of which are incorporated herein by reference. Prodrugs may also be considered to be analogs or derivatives of the compounds of the present invention.

The preparation of the compounds of the present invention may be performed using the standard methods know in the art of organic synthesis. Reaction transformation using compounds having functional groups may be performed on compounds with functional groups that may be protected. A "protected" compound or derivatives means derivatives of a compound where one or more reactive site or sites or functional groups are blocked with protecting groups. Protected derivatives are useful in the preparation of the compounds of the present invention or in themselves, the protected derivatives may be the biologically active agent. An example of a comprehensive text listing suitable protecting groups may be found in T. W. Greene, *Protecting Groups in Organic Synthesis*, 3rd edition, John Wiley & Sons, Inc. 1999.

The synthesis of compounds of Formulae II and III is in Scheme 1. Compound 2 with $R_5$=OEt is commercially available from Acros. Compound 2 with $R_5$=OMe can be prepared from dimethylamine and methyl propiolate according to Navarro-Vazquez et al. *J. Org. Chem.* 2002, 67(10), 3220. The corresponding amides can be prepared as described by Nuvole, A. et al. *J. Chem. Soc. Perkin Trans.* 1, 1989, 1007-1011 and Dabrowski, J. et al. *Tetrahedron,* 1976, 32, 1025-1029.

Intermediate 3 can also be prepared as shown in Scheme 2:

Scheme 2

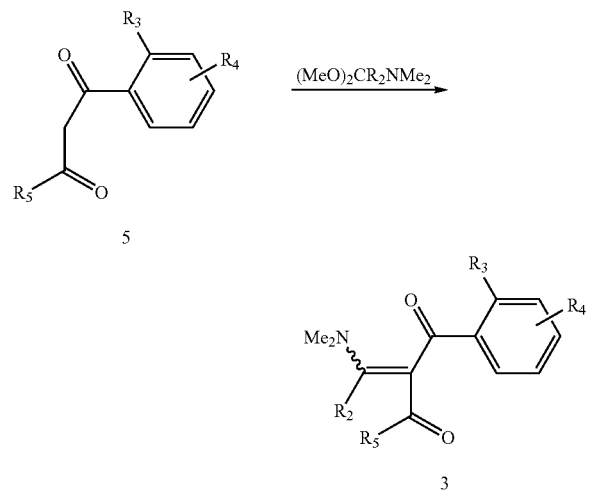

With $R_5$=alkyl, compound 5 can be prepared according to Collins, J. L. et al. U.S. Pat. No. 6,498,174 or by using the method of Atkins, R. J., et al. *Organic Process Research & Development* 1997, 1, 185-197 or Popic, et al. *Synthesis* 1991, 195-198. For $R_5$=alkoxy, compound 5 is prepared according to the method of Oikawa, Y. et al. *J. Org. Chem.* 1978, 43(10), 2087-2088. For $R_5$=NMe$_2$, compound 3 is prepared from 2 ($R_5$=NMe$_2$) by using the method of Grohe, K. U.S. Pat. No. 4,699,992. Compound 5 with $R_5$=amino or alkoxy is prepared as shown in Scheme 3, starting from Meldrum's acid (6), synthesis of acyl Meldrum's acid (7): Yamamoto, Y. et al. Chem. Pharm. Bull. 1987, 35, 1860-70; reaction of acyl Meldrum's acid with amines: Andrews, I. P. et al. *Tetrahedron Lett.* 1995, 36(42), 7743-46; Pak, C. S. et al. Synthesis 1992, 1213-1214; Moya, P. et al. *J. Org. Chem.* 1998, 63, 8530-35.

Scheme 1:

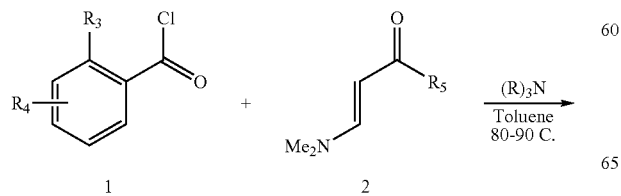

Scheme 3

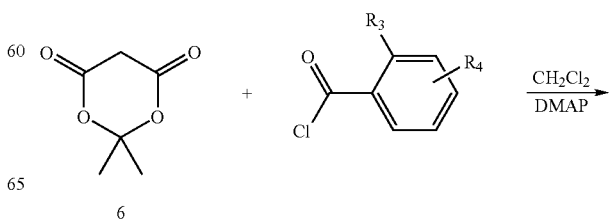

-continued

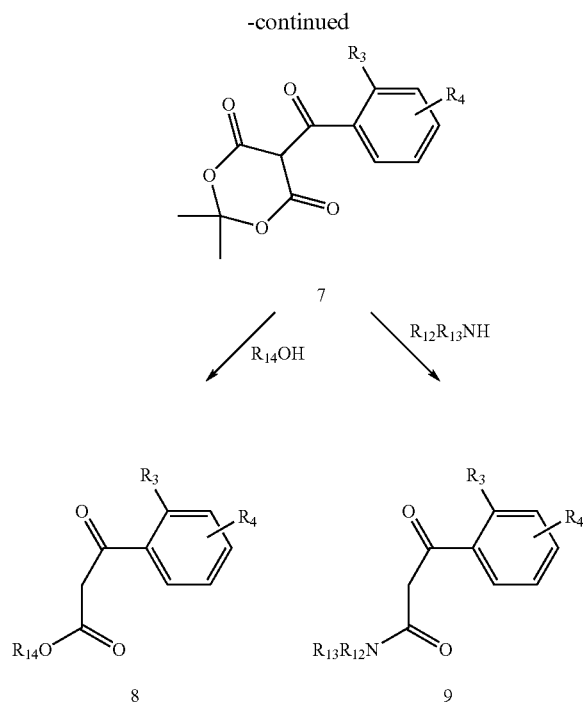

7

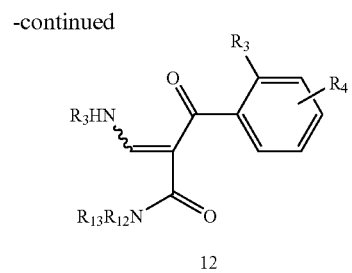

12

Amides (12, Scheme 4) can also be prepared from the corresponding tert-butyl ester (10) prepared as in Scheme 3 above ($R_{14}OH$=tert-butanol). Reaction of the tert-butyl ester with trifluoroacetic acid in the presence of thioanisole gave the acid (11). Standard methods for amide bond formation were then used (isobutyl chloroformate and triethylamine; carbonyl diimidazole, dicyclohexylcarbodiimide, etc.).

Scheme 4

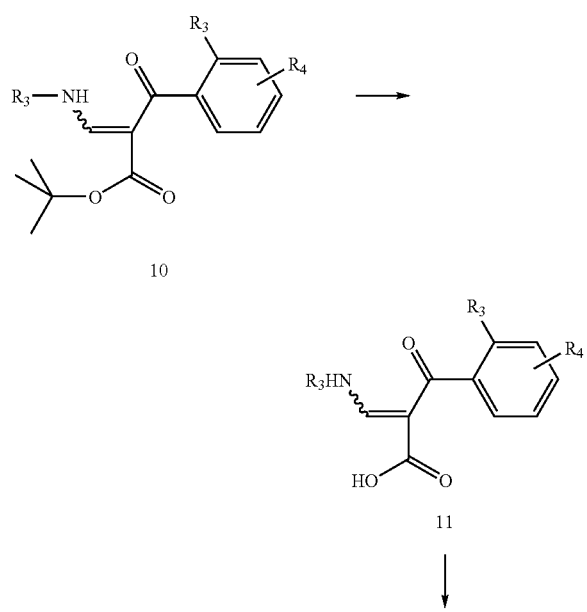

In Vitro Binding Assay 1

[$^{35}$S]TBPS binding assay. The cortex from male Sprague-Dawley rats (weighing 160-200 g) was removed immediately after decapitation and dissected over ice. A $P_2$ homogenate was prepared for binding assay as previously described (Gee, Mol. Pharmacol. 30: 218-225, 1986.). The tissue was homogenized in 0.32 M sucrose (J. T. Baker Chemical Co., Phillipsburg, N.J., USA) with a Teflon-coated pestle, followed by centrifugation at 1,000×g for 10 min. The supernatant was collected and centrifuged at 9,000×g for 20 min. The resultant $P_2$ pellet was resuspended in ice-cold 50 mM sodium potassium phosphate (J. T. Baker) buffer (pH 7.4) containing 200 mM NaCl (J. T. Baker) and used immediately in binding assays. A 2 nM concentration of [$^{35}$S]TBPS (86 Ci/mmol; New England Nuclear, Boston, Mass., USA) was incubated with 100 µl of tissue homogenate (10% w/v) in the presence or absence of 5 µM GABA (Sigma Chem. Co., St. Louis, Mo.) and 5 µl aliquots of test drug dissolved in dimethyl sulfoxide (Sigma Chem. Co.) ($\leq$10 µl of solvent used in all assays). At the concentration ($\leq$1%) used, dimethyl sulfoxide had no effect on specific [$^{35}$S]TBPS binding. All assays were brought to a final volume of 1 ml with 50 mM sodium potassium phosphate buffer (pH 7.4) containing 200 mM NaCl. Non-specific binding was defined as binding in the presence of 2 µM TBPS (NEN, Boston, Mass.) and accounted for ~30% of the total binding. Assays were terminated after a 90-min steady-state incubation at 25° C. by rapid filtration through glass fiber filters (no. 32; Schleicher & Schuell, Keene, N.H.). Filter-bound radioactivity was quantified by liquid scintillation spectrophotometry. The data were evaluated by nonlinear regression (GraphPad, Inc., San Diego, Calif.) to obtain $IC_{50}$ (concentration at which half-maximal inhibition of radioligand occurs) values.

Electrophysiological Assay 1:

Pregnant Sprague-Dawley rats, incubating embryos of 17-19 days gestation, were sacrificed by cervical dislocation. The embryos were removed under aseptic conditions and the brains quickly excised and placed in Hank's balanced salt solution (HBSS, Gibco) at ambient room temperature (18-22° C.). The hippocampi were dissected out and chopped into fragments (~2 mm$^3$) and transferred into an enzyme solution containing (in mM): NaCl 116, KCl 5.4, NaHCO$_3$ 26, NaH$_2$PO$_4$ 1, CaCl$_2$ 1.5, MgSO$_4$ 1, EDTA 0.5, glucose 25, cysteine 1, and papain 20 U/ml (Sigma) and incubated at 37° C., 5% CO$_2$, 100% relative humidity for 1 hr. Tissue fragments were washed in HBSS containing 1 mg/ml of bovine serum albumin (BSA) and 1 mg/ml of ovomucoid (both Sigma). Tissue was transferred into a further 3-4 ml of this solution and gently triturated into a single cell suspension using a fire-polished Pasteur pipette. The single cell suspension was layered on to 5 ml HBSS containing 10 mg/ml of BSA and 10 mg/ml of ovomucoid and centrifuged at 100×g for 10 min. The supernatent was discarded and the cells resuspended in 3-4 ml of glutamine-free minimal essential media (MEM, Gibco) supplemented with heat-inactivated fetal calf serum (5% v/v Gibco), heat-inactivated horse serum (5% v/v Gibco), streptomycin and penicillin (50 µg/ml and 5000 i.u./ml, respectively), glutamine and glucose (final concentrations 2 mM and 20 mM [Gibco and BDH] respectively). Approximately $1-2\times10^5$ cells were plated out on to each 35 mm (Falcon "Primaria") tissue culture dish which contained ~1 ml of the sera-enriched MEM. The plates were maintained at 37° C., in 5% $CO_2$, and 100% relative humidity until used in electrophysiological studies. Background proliferation of non-neuronal elements was suppressed with cytosine arabinoside (10 µM, Sigma) for 48 hr 7 days after initial dissociation.

The compounds of the present invention that evoked membrane currents were recorded from hippocampal neurons using the whole cell configuration of the patch-clamp technique. Neurons were voltaged clamped at 60 mV using a List electronics L/M EPC-7 converter head stage and amplifier. Cells were perfused with an external (bath) recording solution containing (in mM): NaCl 140, KCl 2.8, $MgCl_2$ 2, $CaCl_2$ 1 and HEPES-NaOH 10 (pH 7.2). Tetrodotoxin (TTX, 0.3 µM) was included in the recording solution to suppress synaptic activity. The external solution was delivered (at ~2 ml/min) by a Watson-Marlow flow pump via non-sterile tubing which was connected to a plastic cannula (tip dia 1 mm). The input cannula was mounted on a Prior® micromanipulator and was positioned in close (<1 mm) proximity to the cell under study. Bath solution was withdrawn from the dish via a 19G needle connected by flexible tubing to an aquarium suction pump. The recording electrode was filled with an internal solution composed of (in mM): CsCl or KCl 140, $MgCl_2$ 2, $CaCl_2$ 0.1, EGTA 1.1 (free $Ca^{2+}\sim10^{-8}$ M), HEPES-NaOH 10, and ATP-$Mg^{2+}$ 2. The recording electrodes were fabricated from glasss hematocrit tubes (Kimble sodalime tubes 73811) on a Narishige PB7 two stage electrode puller. Electrodes were coated within 100 µm of the tip with "Sylgard" (Dow Corning) and fire polished just before use. The compounds were applied locally to the soma of a voltage-clamped neuron by pressure ejection (1.4 Kpa, 10-80 msec, 0.1-0.033 Hz) from the tip of a modified recording pipette using a Picospritzer II device (General Valve Corporation). The compound-containing pipette was positioned within 0.1 mm of the cell using a Leitz micromanipulator. The microscope and micromanipulators were all mounted on a vibration-free isolation air table (Wentworth) placed inside a Faraday cage. The compound-evoked whole cell currents were monitored on a storage oscilloscope (Tektronix 2212), recorded, after digital pulse code modulation (frequency response 14 kHz, Sony PCM 701), and displayed on Multitrace (Electromed) pen chart recorder (frequency response 0.5 kHz). All drugs, other than the compounds of the present invention, were applied to cells via the superfusion system. Compound-evoked whole cell currents were measured at their peak. Responses in the presence of drugs expressed as the arithmetic mean±SEM of responses in the absence (control) or drugs.

Electrophysiology Assay 2

$GABA_A$ subunit transfected HEK cells are maintained at 37° C. and 5% $CO_2$ using Dulbecco's Modified Eagle's Medium with L-glutamine and no sodium pyruvate (Irvine Scientific #9031, Irvine Calif.) and supplemented with 10% fetal bovine serum (Irvine Scientific #3000), 10 U/ml hygromycin B (Calbiochem #400051), and an antibiotic cocktail consisting of 100 µg/ml streptomycin sulfate, 0.25 µg/ml amphotericin B, 100 units/ml penicillin G (Gibco 15240-096, Gaithersburg Md.). Cells are passed by 2×wash with phosphate buffered saline (PBS) pH 7.4 and lifted using 1×trypsin/EDTA solution in PBS (0.5 mg/ml trypsin, 0.2 mg/ml EDTA, Irvine Scientific #9342) when confluency reaches ~90%.

$GABA_A$ subunit transfected HEK cells are grown to ~70% confluency on slide. Cells are transferred to a bath that is continuously perfused with extracellular saline. The extracellular medium contained 145 mM NaCl, 3 mM KCl, 1.5 mM $CaCi_2$, 1 mM $MgCi_2$, 5.5 mM d-glucose, and 10 mM HEPES, pH 7.4 at an osmolarity of 320-330 mosM. Recordings are performed at room temperature using the whole cell patch clamp technique. The patch pipette solution contained 147 mM N-methyl-D-lucamine hydrochloride, 5 mM CsCl, 5 mM $K_2ATP$, 5 mM HEPES, 1 mM $MgCi_2$, 0.1 mM $CaCl_2$, and 1.1 mM EGTA, pH 7.2, at an osmolarity of 315 mosM. Pipette-to-bath resistance is typically 3-5 Mohms. Cells are voltage clamped at −60 mV, and the chloride equilibrium potential was approximately 0 mV. Drugs are dissolved in extracellular medium and rapidly applied to the cell by local perfusion. A motor driven multi-channel switching system exchanged solutions in approximately 20 ms.

In vivo Pharmacology

Anticonvulsant assay: Adult male non-Swiss albino (NSA) mice (25-30 g) are used in these studies. Time to peak anticonvulsant effect was determined against picrotoxin (Sigma) induced seizures. Mice were injected with picrotoxin (3.15 mg/kg s.c.) at various time points up to 60 minutes after the injection of drug (30 mg/kg i.p.) and the time that maximum protection was observed was defined as the time of peak effect. 6 Animals were used per dose of test drug. Mice are injected (i.p.) with various doses of drug dissolved in DMSO or vehicle (DMSO 5 µl/g body weight) at time of peak effect before administration (s.c.) of a $CD_{97}$ dose of metrazol (85 mg/kg), (+)-bicuculline (2.7 mg/kg), or picrotoxin (3.15 mg/kg), or vehicle (0.9% saline 5 µl/g body weight). Immediately after the injection mice are observed for a period of 45-60 minutes. The number of animals with tonic/clonic convulsions is recorded.

Vogel Conflict

Adult male rats are randomly divided into groups of 6 rats/group. Animals were deprived of water overnight (16 hr). Food was freely available at time of thirsting. Thirty minutes after injection (i.p.) of test drug, control drug (diazepam), or vehicle control rats are placed in a square plexiglass box containing a stainless steel bottom connected to one side of a drinkometer circuit. At the other side of the drinkometer circuit a water bottle, placed so the drink tube extends into the plexiglass box, is connected. When a subject drinks from the bottle the circuit is closed and an electric shock is delivered at the tube after seven licks are recorded. The number of licks in a 10 min session is recorded.

Light-dark Transition

Male NSA mice (25-30 g) are used. The apparatus consists of an open-topped box divided into small and large area by a partition that has a hole at floor level. The small compartment is painted black and the large compartment white. The white compartment was illuminated with light-and the black compartment with red light. The time spent in the light compartment and the number of transitions between compartments are recorded during a 3 min test session. Vehicle or test compounds are administered 30 min prior to the test. Diazepam is administered (i.p.) at 2 mg/kg.

EXAMPLE 1

Ethyl 2-chloro-α-[(dimethylamino)methylene]-β-oxo-benzenepropanoate

A mixture of ethyl 3,3-dimethylaminoacrylate (4.68 g, 32.7 mmol) and N,N-diisopropylethylamine (12 mL, 8.9 g, 69 mmol) was stirred at rt and a solution of 2-chlorobenzoyl chloride (5.72 g, 32.7 mmol) in 30 mL of toluene was added over 5 mins.

The yellow solution that formed was placed in an oil bath at 85-90° C. After 3 h, the mixture that formed was filtered and the solid was washed with toluene (4×25 mL). The pooled toluene washes were extracted with water (3×50 mL) and brine (1×30 mL), dried ($Na_2SO_4$), filtered and concentrated. The dark filtrate was concentrated and the oily residue was triturated with hexanes (100 mL). The solid that formed was isolated by filtration and washed with hexanes (25 mL). The crude product was dissolved in a minimum volume of EtOAc and added to 16.5 cm of flash silica gel in a 5 cm dia. column. Elution with 100% EtOAc afforded an oil that solidified after trituration with hexanes. The solid, weight 5.68 g (62%), exhibited mp 70-71.5° C.

The following compounds were prepared by using the method described above:
  ethyl 4-chloro-α-[(dimethylamino)methylene]-β-oxo-benzenepropanoate;
  ethyl 2-chloro-α-[(dimethylamino)methylene]-4-fluoro-3-methyl-β-oxo-benzenepropanoate, mp 104.5-106.5° C.;
  ethyl α-[(dimethylamino)methylene]-β-oxo-1-naphthalenepropanoate, oil after flash chromatography with 4:1 hexanes/EtOAc;
  ethyl 2-chloro-α-[(dimethylamino)methylene]-5-nitro-β-oxo-benzenepropanoate (03DJH60B);
  ethyl α-[(dimethylamino)methylene]-2-methyl-β-oxo-benzenepropanoate oil after flash chromatography;
  ethyl 2-bromo-α-[(dimethylamino)methylene]-β-oxo-benzenepropanoate;
  ethyl α-[(dimethylamino)methylene]-β-oxo-2-trifluoromethyl benzenepropanoate; and
  ethyl α-[(dimethylamino)methylene]-2-nitro-β-oxo-benzenepropanoate.

EXAMPLE 2

Methyl 2-chloro-α-[(dimethylamino)methylene]-β-oxo-benzenepropanoate

A mixture of methyl 2-chlorobenzoylacetate (Acros; 266 mg, 1.25 mmol) and N,N-dimethylformamide dimethylacetal (161 mg, 1.35 mmol) was stirred at rt under $N_2$ for 2 weeks. The reaction was then concentrated in vacuo and the residue was adsorbed on silica gel and chromatographed. Elution with 3:1 EtOAc/hexanes afforded 193 mg of the title compound as a yellow solid.

EXAMPLE 3

1,1-Dimethylethyl 2-chloro-α-[[(4-iodophenyl)amino]methylene]-β-oxo-benzenepropanoate 1,1-Dimethylethyl 2-chlorobenzoylacetate. A solution of 5-(2-chlorobenzoyl)-2,2-dimethyl-1,3-dioxane-4,6-dione (539 mg, 1.91 mmol) in 17 mL of toluene was treated with 0.6 mL (465 mg, 6.27 mmol) of 2-methyl-2-propanol and heated at 80-85° C. After 4.5 h, the reaction was allowed to cool and concentrated in vacuo. The crude product was adsorbed onto 2 g of flash silica and added to 22.5 cm of flash silica in a 2 cm dia. column. Elution with 9:1 hexanes/EtOAc gave 416 mg (86%) of the β-ketoester as an oil.

1,1-Dimethylethyl 2-chloro-α-[(dimethylamino)methylene]-β-oxo-benzenepropanoate. 1,1-Dimethylethyl 2-chlorobenzoylacetate (87 mg, 0.342 mmol) and N,N-dimethylformamide dimethyl acetal (50 μL, 45 mg, 0.375 mmol) were stirred in 1 mL of toluene. After 6 d, the reaction was concentrated in vacuo and the residue was subjected to flash chromatography. Elution with 1:1 hexanes/EtOAc afforded 61 mg (58%) of the title compound as an oil that solidified on standing, mp 97-99° C.

1,1-Dimethylethyl 2-chloro-α-[[(4-iodophenyl)amino]methylene]-β-oxo-benzenepropanoate. A solution of 1,1-dimethylethyl 2-chloro-α-[(dimethylamino)methylene]-β-oxo-benzenepropanoate (25.5 mg, 0.082 mmol) in 1 mL of toluene was treated with 4-iodoaniline (17.9 mg, 0.082 mmol) added as a solid in one portion. After stirring overnight, the reaction was concentrated in vacuo and the residue was adsorbed onto silica gel and added to 19.5 cm of flash silica in a 2 cm dia. column. Elution with 5:1 hexanes/EtOAc gave the title compound as a solid.

EXAMPLE 4

2-Chloro-α-[[(4-cyanophenyl)amino]methylene]-β-oxo-N-propyl-benzenepropanamide 5-(2-Chlorobenzoyl)-2,2-dimethyl-1,3-dioxane-4,6-dione. A solution of 4-(dimethylamino)pyridine (33.96 g; 278 mmol) and 2,2-dimethyl-1,3-dioxane-4,6-dione (20.0 g, 139 mmol) in 50 mL of $CH_2Cl_2$ was cooled in an ice-salt bath to −10° C. A solution of 2-chlorobenzoyl chloride (29.2 g, 167 mmol) in 20 mL of $CH_2Cl_2$ was added dropwise via addition funnel over 1 h. After stirring cold for 1 h, the reaction was allowed to warm to rt and stirred for an additional 3 h. The resulting yellow-orange solution was then extracted with an aq. 10% HCl solution (200 mL) and 200 mL of brine. After drying with $MgSO_4$, the mixture was filtered and the solvent was removed in vacuo. The resulting orange oil was triturated with hexanes (3×50 mL), affording the title compound (20 g) as a yellow solid.

2-Chloro-β-oxo-N-propylbenzenepropanamide. A suspension of 5-(2-chlorobenzoyl)-2,2-dimethyl-1,3-dioxane-4,6-dione (2.06 g, 7.30 mmol) in 100 mL of toluene was treated with neat propylamine (550 μL, 395 mg, 6.70 mmol) added dropwise via syringe. The reaction was then heated at 80-90° C. for 4 h. Once at rt, the reaction was concentrated to dryness. The residue was adsorbed onto flash silica gel and added to 19 cm of flash silica gel in a 5 cm dia. column. Elution with 4:1 hexanes/EtOAc afforded 851 mg (53%) of the title compound as a yellow oil.

2-Chloro-α-[(dimethylamino)methylene]-β-oxo-N-propylbenzenepropanamide. A solution of 789 mg (3.29 mmol) of 2-chloro-β-oxo-N-propyl-benzenepropanamide in 5 mL of $CH_2Cl_2$ was treated with neat N,N-dimethylformamide dimethylacetal (450 μL, 402 mg, 3.38 mmol) added dropwise via syringe. The reaction was allowed to stir overnight and then concentrated in vacuo. Flash chromatography (11 cm in a 5 cm column) eluting with 2% $MeOH/CH_2Cl_2$ afforded 756 mg (79%) of the title compound as a yellow foam. Trituration with hexanes gave a yellow solid, mp 76-78° C.

2-Chloro-β-oxo-N-propyl-α-[[[(4-trifluoromethyl)phenyl]amino]methylene]-benzenepropanamide. To 2-chloro-α-[(dimethylamino)methylene]-β-oxo-N-propylbenzenepropanamide (63.5 mg, 0.215 mmol) was added 4-(trifluoromethyl)aniline (27 μL, 34.6 mg, 0.215 mmol) and toluene (3 mL). The mixture was heated at reflux for 3 h. Once at rt, the reaction was concentrated in vacuo. The residue was adsorbed onto flash silica gel and added to 20 cm of flash silica gel in a 2 cm dia. column. Elution with 6:1 hexanes/ EtOAc afforded 57 mg the desired product as a solid, mp 96-97.5° C.

The following compounds were prepared by using the method described above:

5-(2-chloro-4-fluoro-3-methylbenzoyl)-2,2-dimethyl-1,3-dioxane-4,6-dione, yellow-orange solid after trituration with hexanes;

2-chloro-β-oxo-N-propylbenzenepropanamide, light yellow oil after chromatography with 4:1 hexanes/EtOAc;

2-chloro-N-ethyl-β-oxobenzenepropanamide, light yellow oil after chromatography with 4:1 hexanes/EtOAc;

4-chloro-β-oxo-N-propylbenzenepropanamide, light yellow solid after chromatography with 1.5:1 hexanes/ EtOAc;

2-fluoro-β-oxo-N-propylbenzenepropanamide, light brown oil after chromatography with 1.5:1 hexanes/ EtOAc;

2-chloro-α-[(dimethylamino)methylene]-N-ethyl-β-oxo-N-benzenepropanamide, light yellow solid, mp 97.5-100° C. after chromatography with 2.5% MeOH/ $CH_2Cl_2$;

2,2-dimethyl-5-(2-methylbenzoyl)-1,3-dioxane-4,6-dione, red-orange semisolid after trituration with hexanes;

2-methyl-β-oxo-N-propyl-benzenepropanamide, light yellow oil after chromatography with 2:1 hexanes/ EtOAc;

2-methyl-β-oxo-N-(2-propynyl)-benzenepropanamide, light yellow oil after chromatography with 2:1 hexanes/ EtOAc;

α-[(dimethylamino)methylene]-2-methyl-β-oxo-N-propyl-benzenepropanamide, light yellow oil after chromatography with 2.5% MeOH/$CH_2Cl_2$;

α-[(dimethylamino)methylene]-2-methyl-β-oxo-N-(2-propynyl)-benzenepropanamide, light yellow oil after chromatography with 2.5% MeOH/$CH_2Cl_2$. $^1$H NMR (500 MHz, $CDCl_3$) δ8.97 (br s, 1H), 7.29-7.14 (m, 5H), 4.16 (dd, 2H, J=5.3, 2.5 Hz), 3.03 (br s, 6H), 2.31 (s, 3H), 2.20 (t, 1H, J=2.5 Hz);

2-chloro-α-[[(4-iodophenyl)amino]methylene]-β-oxo-N-propyl-benzenepropanamide;

2-chloro-N-ethyl-α-[[(4-iodophenyl)amino]methylene]-β-oxo-benzenepropanamide; $^1$H NMR (500 MHz, $CDCl_3$) δ 12.96 (d, 1H, J=12.2 Hz), 9.52 (br s, 1H), 7.66 (d, 1H, J=12.5 Hz), 7.60 (d, 2H, J=8.5 Hz), 7.47 (d, 1H, J=7.9 Hz), 7.41 (dt, 1H, J=7.6, 1.5 Hz), 7.37 (dt, 1H, J=7.4, 0.7 Hz), 7.31 (d, 1H, J=7.4, 1.7 Hz), 6.66 (d, 2H, J=8.6 Hz), 3.46 (br s, 2H), 1.29 (t, 3H, J=7.3Hz);

α-[[(4-ethynylphenyl)amino]methylene]-2-methyl-β-oxo-N-propyl-benzenepropanamide, mp 160-161.5° C. after chromatography with 7:1 hexanes/EtOAc ($R_f$ 0.36). $^1$H NMR (500 MHz, $CDCl_3$)δ 12.90 (d, 1H, J=12.6 Hz), 9.73 (br s, 1H), 7.77 (d, 1H, J=12.5 Hz), 7.40 (d, 2H, J=8.7 Hz), 7.36 (dt, 1H, J=7.5, 1.4 Hz), 7.29-7.25 (m, 2H), 7.21 (d, 1H, J=6.3 Hz), 6.79 (d, 2H, J=8.7 Hz), 3.40 (q, 2H, J=6.5 Hz), 3.07 (s, 1H), 2.32 (s, 3H), 1.69 (sextet, 2H, J=7.3 Hz), 1.04 (t, 3H, J=7.4 Hz). Anal Calcd. for $C_{22}H_{22}N_2O_2$: C, 76.28; H, 6.40; N, 8.09. Found: C, 76.09; H, 6.45; 7.91.;

α-[[(4-ethynylphenyl)amino]methylene]-2-methyl-β-oxo-N-(2-propynyl)-benzenepropanamide;

α-[[(4-cyanophenyl)amino]methylene]-2-methyl-β-oxo-N-propyl-benzenepropanamide;

α-[[(1-azabicyclo[3.3.0]octyl)-1-amino]methylene]-2-chloro-β-oxo-N-propyl-benzenepropanamide, mp 111.5-113° C. after chromatography with 5:1 hexanes/ EtOAc ($R_f$ 0.34);

2-chloro-α-[[(4-ethynylphenyl)amino]methylene]-β-oxo-N-propyl-benzenepropanamide;

2-chloro-α-[[(4-fluorophenyl)amino]methylene]-β-oxo-N-propyl-benzenepropanamide, mp 95-96° C.;

2-chloro-α-[[(4-iodophenyl)amino]methylene]-β-oxo-N-(2-propynyl)-benzenepropanamide;

2-chloro-N-ethyl-β-oxo-α-[(pyrazinyl)amino]-benzenepropanamide, white solid, mp 134.5-137° C. after chromatography with 2% MeOH/$CH_2Cl_2$ ($R_f$ 0.6);

2-chloro-α-[(isoxazolyl-3-amino)methylene]-β-oxo-N-propyl-benzenepropanamide, white solid, mp 116.5-118.5° C. after chromatography with 1% MeOH/ $CH_2Cl_2$;

2-chloro-N-ethyl-α-oxo-α-[(1,2,4-triazolyl-4-amino)methylene]-benzenepropanamide, white solid that precipitated from toluene, washed twice with toluene, mp 189.5-19° C.;

2-chloro-N-ethyl-α-[(isoxazolyl-3-amino)methylene]-β-oxo-benzenepropanamide, white solid, mp 139-140° C. after chromatography with 2% MeOH/$CH_2Cl_2$ ($R_f$ 0.7); and 2-chloro-α-[(4-ethynylphenyl)aminomethylene] -β-oxo-N-propyl-1-naphthalenepropanamide, off white solid, mp 155-156° C. after chromatography with 8:1 hexanes/EtOAc ($R_f$ 0.25).

EXAMPLE 5

Ethyl 2-chloro-α-[[(3-chloro-4-fluorophenyl)amino] methylene]-β-oxo-benzenepropionate A solution of ethyl 2-chloro-α-[(dimethylamino)methylene]-β-oxo-benzenepropanoate (50 mg, 0.177 mmol) in 1 mL of EtOH was treated with neat 3-chloro-4-fluoroaniline (25.8 mg, 0.177 mmol). After stirring at rt until complete by TLC, the reaction was concentrated in vacuo. The residue was subjected to flash chromatography (1:1 EtOAc/hexanes), affording 42.6 mg (63%) of the product as a white solid, mp 96-102° C. $^1$H NMR (400 MHz, $CDCl_3$ 9:1 ratio of alkene isomers, major isomer NMR given) δ12.66 (d, 1H, J=12.8 Hz), 8.50 (d, 1H, J=13.2 Hz), 7.37-7.16 (m, 7H), 4.01 (q, 2H, J=7.1 Hz), 0.93 (t, 2H, J=7.1 Hz).

EXAMPLE 6

Ethyl 2-chloro-α-oxo-α-[[(4-phenylbutyl)amino] methylene]-benzenepropionate

A solution of 4-phenylbutylamine (24.5 mg, 0.164 mmol) in 1 mL of EtOH was treated with solid ethyl 2-chloro-α-[(dimethylamino)methylene]-β-oxo-benzenepropanoate (46.5 mg, 0.165 mmol). After stirring at rt for 5 m, the reaction was concentrated in vacuo and the residue was subjected to flash chromatography, (10 cm of silica gel in a 2 cm dia. column; elution with 100% $CH_2Cl_2$), affording 60.4 mg (96%) of the title compound as a white solid, mp 90-92° C. By 1H NMR the compound is a 4.5:1 mixture of double bond isomers. 1H NMR ($CDCl_3$, 400 MHz) major isomer δ 11.06 (br m, 1H), 8.11 (d, 1H, J=14.0 Hz), 7.34-7.17 (m, 9H), 3.94 (q, 2H, J=7.1 Hz), 3.43 (m, 2H), 2.68 (m, 2H), 1.73 (m, 4H), 0.88 (t, 3H, J=7.1 Hz). $^1$H NMR ($CDCl_3$, 400 MHz) minor isomer (only peaks that are shifted from major isomer are given) δ9.52 (br m, 1H), 8.17 (d, 1H, J=9.4 Hz), 3.89 (q, 2H, J=7.1 Hz), 0.77 (t, 3H, J=7.1 Hz).

EXAMPLE 7

Ethyl 2-chloro-β-oxo-α-[[[4-(1,2,3,4-tetrahydronaphthyl-1-amino)phenyl]amino]methylene]-benzenepropionate 4-(1,2,3,4-Tetrahydronaphthyl-1-amino)nitrobenzene. A solution of 4-fluoro-1-nitrobenzene (2.82 g, 20.0 mmol) in 10 mL of DMSO was treated with neat 1,2,3,4-tetrahydro-1-aminonaphthalene (3.0 mL, 3.08 g, 20.9 mmol) added dropwise via syringe. The resulting orange solution was stirred at rt. After 6 d, the reaction was added to cold water/EtOAc. The aq. layer was washed with EtOAc (3×50 mL) and the pooled organic layers were washed with 100 mL of a 0.7 M aq. HCl solution, water and brine. After drying (Na$_2$SO$_4$), the mixture was filtered and the solvent removed in vacuo. The residue was triturated with 100 mL of hexanes, giving 2.35 g of the desired product as a bright yellow solid.

4-(1,2,3,4-Tetrahydronaphthyl-1-amino)aniline. A suspension of nitro compound (1.06 g, 3.93 mmol) in 115 mL of glacial HOAc was treated with solid Zn metal (1.32 g, 20.2 mmol) added in portions. After 25 m, an additional 1.14 g of Zn was added. After 30 m, the mixture was filtered. The solid was washed with HOAc (2×25 mL). The HOAc was then removed in vacuo and the residue was partitioned between EtOAc and a half saturated aq. NaHCO$_3$ solution (50 mL of each). The organic layer was separated, washed with 25 mL each of a half saturated aq. NaHCO$_3$ solution and brine, dried (Na$_2$SO$_4$), filtered and concentrated to dryness. The aniline (891 mg, 95%) was isolated as an air sensitive solid.

Ethyl 2-chloro-β-oxo-α-[[[4-(1,2,3,4-tetrahydronaphthyl-1-amino)phenyl]amino]methylene]-benzenepropionate. A solution of ethyl 2-chloro-α-[(dimethylamino)methylene]-β-oxo-benzenepropanoate (1.027 g, 3.65 mmol) in EtOH (10 mL) and 4-(1,2,3,4-tetrahydronaphthyl-1-amino)aniline (869 mg, 3.65 mmol) was as added as a solid in one portion. After stirring at rt for 4 d, the solid precipitate that formed was isolated by filtration and washed with EtOH (3×10 mL). The yellow-green solid that resulted was adsorbed onto flash silica gel and subjected to column chromatography. Elution with 6:1 hexanes/EtOAc gave a yellow oil. Trituration with hexanes gave 623 mg (36%) of a yellow solid, mp 118-121° C. $^1$H NMR (400 MHz, CDCl$_3$ 4.6:1 ratio of alkene isomers, major isomer NMR given) δ 12.87 (d, 1H, J=13.7 Hz), 8.54 (d, 1H, J=13.7 Hz), 7.38-7.17 (m, 8H), 7.14 (d, 2H, J=8.8 Hz), 6.69 (d, 2H, J=8.7 Hz), 4.63 (m, 1H), 4.04-3.94 (m, 4H), 2.90-2.74 (m, 2H), 2.01-1.80 (m, 4H), 0.92 (t, 3H, J=7.1 Hz).

The following compounds were prepared as described in the foregoing examples:

Ethyl 2-chloro-α-[[(4-ethynylphenyl)amino]methylene]-β-oxo-benzenepropionate, mp 128.5-133° C.;
  ethyl 2-bromo-α-[[(4-fluorophenyl)amino]methylene]-β-oxo-benzenepropionate, mp 83.5-84.5° C.;
  ethyl α-[(benzyl)aminomethylene]β-oxo-1-naphthalenepropionate, mp 142-143.5° C.;
  ethyl β-oxo-α-[(2-phenylethyl)aminomethylene]-1-naphthalenepropionate, mp 131-133° C.;
  ethyl β-oxo-α-[(3-phenylpropyl)aminomethylene]-1-naphthalenepropionate, mp 86-88° C.;
  ethyl α-[(octyl)aminomethylene]-β-oxo-1-naphthalenepropionate, mp 88-89° C.;
  ethyl α-[(octyl)aminomethylene]β-oxo-1-naphthalenepropionate, mp 72-73° C.;
  ethyl 2-methyl-β-oxo-α-[(4-phenylbutyl)aminomethylene]-benzenepropionate. mp 87-88° C.;
  ethyl 2-nitro-β-oxo-α-[(4-phenylbutyl)aminomethylene]-benzenepropionate, mp 120-121.5° C.;
  ethyl α-[[(4-fluorophenyl)amino]methylene]-2-nitro-β-oxo-benzenepropionate, mp 109-110° C.;
  ethyl α-[[(4-iodophenyl)amino]methylene]-β-oxo-2-trifluoromethyl-benzene-propionate, mp 110-111° C.;
  ethyl α-[[(4-methoxyphenyl)amino]methylene]β-oxo-2-trifluoromethyl-benzene-propionate, mp 80-83° C.;
  ethyl 2-chloro-α-oxo-α-[(4-phenylbutyl)aminomethylene]-benzenepropionate, mp 91-92° C.;
  ethyl 2-bromo-α-oxo-α-[(4-phenylbutyl)aminomethylene]-benzenepropionate, mp 96-97° C.;
  ethyl β-oxo-α-[(4-phenylbutyl)aminomethylene]-2-trifluoromethyl-benzenepropionate, mp 104-106° C.;
  ethyl 2-chloro-α-[[(2-naphthyl)amino]methylene]-β-oxo-benzenepropionate, mp 121-122° C.;
  ethyl 2-chloro-α-[[[(3,4-methylenedioxy)phenyl]amino]methylene]β-oxo-benzenepropionate, mp 99-101° C.;
  ethyl 2-chloro-α-[[(4-iodophenyl)amino]methylene]-β-oxo-benzenepropionate (05DJH133A; RMG 20062). Prepared as a 23:1 mixture of double bond isomers, mp 152-153° C. $^1$H NMR (CDCl$_3$, 400 MHz) major isomer δ12.65 (d, 1H, J=13.1 Hz), 8.58 (d, 1H, J=13.4 Hz), 7.73 (d, 2H, J=8.5 Hz), 7.37-7.24 (m, 4H), 7.04 (d, 2H, J=8.6 Hz), 4.01 (q, 2H, J=7.1 Hz), 0.93 (d, 3H, J=7.1Hz);
  methyl 2-chloro-α-[[(4-iodophenyl)amino]methylene]-β-oxo-benzenepropionate, mp 159.5-160.5° C.;
  ethyl 2-chloro-β-oxo-α-[[[(2-phenoxy)ethyl]amino]methylene]-benzenepropionate, mp 134.5-135.5° C.;
  ethyl 2-chloro-α-[[(1-methyl-3-phenylpropyl)amino]methylene]-β-oxo-benzenepropionate, mp 82.5-85° C.;
  ethyl 2-chloro-β-oxo-α-[[[(2-phenylamino)ethyl]amino]methylene]-benzenepropionate (05DJH151C);
  ethyl 2-chloro-α-[[(4-hydroxyphenyl)amino]methylene]-β-oxo-benzenepropionate, mp 197.5-198.5° C.;
  ethyl 2-chloro-α-[[(4-chlorophenyl)amino]methylene]-β-oxo-benzenepropionate, mp 121.5-122.5° C.;
  ethyl 2-chloro-α-[[(3-chlorophenyl)amino]methylene]-β-oxo-benzenepropionate (05DJH110A);
  ethyl 2-chloro-α-[[(2-chlorophenyl)amino]methylene]-β3-oxo-benzenepropionate (05DJH110A);
  ethyl 2-chloro-α-[[(4-methylphenyl)amino]methylene]-β-oxo-benzenepropionate, mp 106-108° C.;
  ethyl 2-chloro-α-[[(4-methoxylphenyl)amino]methylene]-β-oxo-benzenepropionate, mp 96-97° C.;
  ethyl 2-chloro-α-[[(4-isopropylphenyl)amino]methylene]-β-oxo-benzenepropionate, mp 83-85° C.;
  ethyl α-[[(4-butylphenyl)amino]methylene]-2-chloro-β-oxo-benzenepropionate (05DJH108D);
  ethyl 2-chloro-β-oxo-β-[[(4-trifluoromethylphenyl)amino]methylene]-benzenepropionate, mp 127-131° C.;
  ethyl 2-chloro-α-[[(4-ethylphenyl)amino]methylene]-β-oxo-benzenepropionate, mp 80-84° C.;
  ethyl 2-chloro-α-[[[(4-methylthio)phenyl]amino]methylene]-β-oxo-benzenepropionate, mp 127-128° C.;
  ethyl 2-chloro-α-[[[4-(methylsulfinyl)phenyl]amino]methylene]-β-oxo-benzenepropionate and ethyl 2-chloro-α-[[[4-(methylsulfonyl)phenyl]amino]-methylene]-β-oxo-benzenepropionate.

Reaction of ethyl 2- chloro-α-[[[(4-methylthio)phenyl]amino]methylene]-β-oxo-benzenepropionate with 1.5 eq. of 3-chloroperoxybenzoic acid gave a mixture of the corresponding sulfoxide and sulfone which were separated by chromatography (2% MeOH/CH$_2$Cl$_2$);

ethyl 2-chloro-α-[[(4-propylphenyl)amino]methylene]-β-oxo-benzenepropionate;

ethyl 2-chloro-β-oxo-α-[[(4-trifluoromethoxyphenyl)amino]methylene]-benzenepropionate, mp 98.5-103.5° C.; and ethyl α-[[(4-butylphenyl)amino]methylene]-2-nitro-β-oxo-benzenepropiona

EXAMPLE 8

2-Chloro-α-[[(4-iodophenyl)amino]methylene]-Poxobenzenepropanoic Acid

A solution of 1,1-dimethylethyl 2-chloro-α-[[(4-iodophenyl)amino]methylene]-β-oxo-benzenepropanoate (17.9 mg, 0.037 mmol) in $CH_2Cl_2$ was treated with thioanisole (17.5 μL, 18.5 mg, 0.15 mmol) and trifluoroacetic acid (35 μL, 52 mg, 0.454 mmol) at 0° C. The reaction was stirred at rt for 45 m and concentrated in vacuo. The residue was purified by flash chromatography (2.5% MeOH/$CH_2Cl_2$), affording 13 mg of the acid as a white solid, mp 202.5-205° C. MS 450 (M+Na$^+$) 100, 428 (M$^+$) 27.

EXAMPLE 9

2-Chloro-N,N-dimethyl-α-[[(4-iodophenyl)amino]methylene]-β-oxobenzenepropanamide To a suspension of 2-chloro-α-[[(4-iodophenyl)amino]methylene]-β-oxobenzenepropanoic acid (43 mg, 0.10 mmol) in 1 mL of $CH_2Cl_2$ was added N,N'-dicyclohexylcarbodiimide (21 mg, 0.10 mmol). The mixture was cooled in an ice bath and 50 μL (0.10 mmol) of a 2M solution of dimethylamine in THF was added. The reaction mixture was stirred at rt for 16 h. The formed DCU was removed by filtration. The filtrate was washed with water and evaporated to dryness. The title compound (22 mg, 50%) was isolated by column chromatography (5% MeOH in $CH_2Cl_2$); MS 410 (M−45), 455 (M+1), 477(M+Na$^+$).

The following compounds were prepared as described in the foregoing examples:

2-Chloro-N-[(2-dimethylamino)ethyl)]-α-[[(4-iodophenyl)amino]methylene]-β-oxobenzenepropanamide, mp 145-147° C., MS: 497 (100); 520 (22).

EXAMPLE 10

1,3-Diphenyl-2-[(4-iodophenyl)amino)methylene]-1,3-propanedione

2-[(Dimethylamino)methylene]-1,3-diphenyl-1,3-propanedione: To a solution of dibenzoylmethane (1.072 g, 4.78 mmol) in 6 mL of toluene was added neat N,N-dimethylformamide dimethylacetal (0.7 mL, 630 mg, 5.25 mmol) dropwise via syringe. The resulting solution was stirred at rt for 1 h and then heated at reflux for 16 h. Once at rt, the reaction was concentrated in vacuo. The residue was dissolved in a minimum of $CH_2Cl_2$ and added to 13 cm of flash silica gel in a 5 cm dia. column. Elution with 1 L of 1%, 500 mL of 2% and 300 mL of 3% MeOH/$CH_2Cl_2$ gave 975 mg of the desired product as a semisolid. Trituration with 50 mL of hexanes gave 772 mg of the title compound as a light yellow solid, mp 123-124° C. (lit mp 120° C., Schenone, P. et al. *J. Het. Chem.* 1982,19(6), 1355-61).

1,3-Diphenyl-2-[[(4-iodophenyl)amino]methylene]-1,3-propanedione: A solution of 1,3-diphenyl-2-[(dimethylamino)methylene]-1,3-propanedione (317 mg, 1.13 mmol) in 5.5 mL of MeOH was treated with solid 4-iodoaniline (245 mg, 1.12 mmol). The resulting solution was stirred at rt overnight. The resulting precipitate was isolated by filtration and washed with MeOH. The title compound was isolated as a light yellow solid.

Additional compounds prepared are as follows:

α-[[(4-chlorophenyl)amino]methylene]-N-isopropyl-β-oxobenzenepropanamide;

4-chloro-α-[[(4-ethoxyphenyl)amino]methylene]-N-propyl-β-oxobenzene-propanamide;

α-[[(4-chlorophenyl)amino]methylene]-N-isopropyl-β-oxobenzenepropanamide; $^1$H NMR (400 MHz, CDCl$_3$) δ12.83 (d, 1H, J=12.4 Hz), 9.50 (d, 1H, J=6.5 Hz), 7.93 (d, 1H, J=12.4 Hz), 7.53-7.44 (m, 5H), 7.25 (d, 2H, J=8.7 Hz), 6.85 (d, 2H, J=8.7 Hz), 4.19 (octet, 1H, J=6.7 Hz), 1.28 (d, 6H, J=6.4 Hz).

2-chloro-α-[[(4-chlorophenyl)amino]methylene]-N-isopropyl-β-oxobenzene-propanamide; TOF MS ES+m/z 399, 401 (M+Na$^+$);

2-chloro-α-[[(4-chlorophenyl)amino]methylene]-N-ethyl-β-oxobenzenepropanamide; TOF MS ES+m/z 285, 287 (M+Na$^+$);

2-chloro-α-[[(4-ethoxyphenyl)amino]methylene]-N-ethyl-β-oxobenzene-propanamide; $^1$H NMR (400 MHz, CDCl$_3$) δ12.89 (d, 1H, J=12.5 Hz), 9.59 (s, 1H), 7.60 (d, 1H, J=12.7 Hz), 7.46-7.29 (m, 4H), 6.82 (m, 4H), 3.96 (q, 2H, J=7.0 Hz), 3.45 (br m, 2H), 1.38 (t, 3H, J=6.9 Hz), 1.28 (t, 3H, J=7.2 Hz);

2-chloro-α-[[(4-chlorophenyl)amino]methylene]-N-propyl-β-oxobenzene-propanamide; TOF MS ES+m/z 399, 401 (M+Na$^+$);

2-chloro-α-[[(4-chlorophenyl)amino]methylene]-N-(1-methylpropyl)-β-oxobenzene-propanamide; (07TBCJ71) $^1$H NMR (400 MHz, CDCl$_3$) δ 13.00 (d, 1H, J=12.2 Hz), 9.46 (d, 1H, J=7.6 Hz), 7.64 (d, 1H, J=12.4 Hz), 7.48-7.24 (m, 6H), 6.83 (d, 2H, J=8.8Hz), 4.04 (m, 1H), 1.63 (m, 2H), 1.27 (d, 3H, J=6.6 Hz), 1.00 (t, 3H, J=7.6 Hz). TOF MS ES+m/z 413, 415 (M+Na$^+$);

2-chloro-N-ethyl-α-[[(α-methyl-4-fluorobenzyl)amino]methylene]-β-oxobenzene-propanamide;

2-chloro-N-ethyl-α-[[(α-methylbenzyl)amino]methylene]-β-oxobenzene-propanamide;

2-chloro-N-propyl-α-[(2-methyl-1-phenylhydrazino)methylene]-β-oxobenzene-propanamide;

2-chloro-α-[[(4-iodophenyl)amino]methylene]-N-methyl-β-oxobenzene-propanamide; $^1$H NMR (400 MHz, CDCl$_3$) δ 12.94 (d, 1H, J=12.4 Hz), 9.48 (br s, 1H), 7.65 (d, 1H, J=12.4 Hz), 7.60 (d, 2H, J=8.7 Hz), 6.65 (d, 2H, J=8.7 Hz), 2.97 (d, 3H, J=4.6 Hz);

2-chloro-α-[[(4-chlorophenyl)amino]methylene]-N-methyl-β-oxobenzene-propanamide; TOF MS ES+m/z 371, 373 (M +Na+);

2-chloro-α-[[(4-chlorophenyl)amino]methylene]-N-(α-methylbenzyl)-β-oxobenzene-propanamide;

α-[[(4-chlorophenyl)amino]methylene]-N-isopropyl-β-oxobenzenepropanamide; $^1$H NMR (400 MHz, CDCl$_3$) δ12.83 (d, 1H, J=12.4 Hz), 9.50 (d, 1H, J=6.5 Hz), 7.93 (d, 1H, J=12.4 Hz), 7.53-7.44 (m, 5H), 7.25 (d, 2H, J=8.7 Hz), 6.85 (d, 2H, J=8.7 Hz), 4.19 (octet, 1H, J=6.7 Hz), 1.28 (d, 6H, J=6.4 Hz).

4-chloro-α-[[(4-ethoxyphenyl)amino]methylene]-N-propyl-β-oxobenzene-propanamide;

TABLE 1

Inhibition of [$^{35}$S]TBPS binding by Enaminones

| Compound | [$^{35}$S]TBPS IC$_{50}$ (μM) | I$_{max}$ (%) |
| --- | --- | --- |
| ethyl 2-chloro-α-[[(4-ethynylphenyl)-amino]methylene]-β-oxobenzenepropionate | 0.01 | 95 |
| ethyl 2-chloro-α-[[(4-iodophenyl)-amino]methylene]-β-oxobenzenepropionate | 0.02 | 86 |
| α-[[(4-ethynylphenyl)amino]methylene]-2-methyl-β-oxo-N-propyl-benzenepropanamide | 0.02 | 95 |
| ethyl 2-chloro-α-[[(4-cyanophenyl)-amino]methylene]-β-oxobenzenepropionate | 0.06 | 100 |
| 2-methyl-α-[[(4-methylphenyl)amino]methylene]-β-oxo-N-propyl-benzenepropanamide | 0.10 | 100 |
| ethyl α-[(4-fluorophenyl)amino]methylene]-β-oxo-1-naphthalenepropionate | 0.20 | 81 |
| ethyl 2-chloro-α-[[(2-chlorophenyl)-amino]methylene]-β-oxobenzenepropionate | 0.42 | 100 |

What is claimed is:

1. A compound comprising the Formula I:

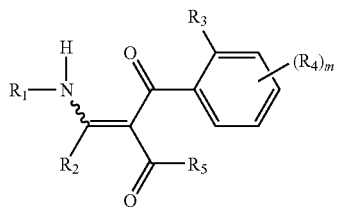

or a pharmaceutically acceptable salt thereof, wherein:
$R_1$ is selected from the group consisting of aryl, heteroaryl and aralkyl, each unsubstituted or substituted;
$R_2$ is selected from the group consisting of hydrogen and unsubstituted or substituted $C_{1-10}$alkyl;
$R_3$ is selected from the group consisting of fluoro, chloro, bromo, iodo, $C_{1-10}$alkoxy, nitro, halo$C_{1-10}$alkyl, perhalo$C_{1-10}$alkyl and unsubstituted or substituted $C_{1-10}$alkyl;
each $R_4$ is independently selected from the group consisting of halogen, nitro, $C_{1-10}$alkyl, $C_{2-10}$alkenyl, $C_{2-10}$alkynyl, $C_{1-10}$alkoxy, aralkyl, aryl, heteroaryl, cycloalkyl and heterocycloalkyl, each unsubstituted or substituted, or wherein $R_3$ and an adjacent $R_4$ together form a fused unsubstituted or substituted 5 or 6 membered cycloalkyl, aryl or heteroaryl ring;
$R_5$ is selected from the group consisting of —NH$_2$, $C_{1-10}$alkylamino, di($C_{1-10}$)alkylamino and aryl, each substituted or unsubstituted; and
m is 0, 1, 2, 3 or 4.

2. A compound according to claim 1: wherein:
$R_5$ is selected from the group consisting of —NH$_2$, $C_{1-10}$alkylamino, di($C_{1-10}$)alkylamino and aryl, each unsubstituted or substituted.

3. A compound comprising the Formula Ib:

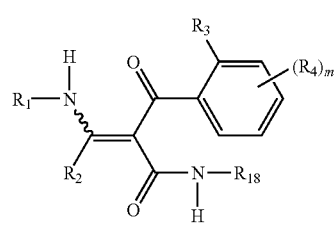

or a pharmaceutically acceptable salt thereof, wherein:
$R_1$ is selected from the group consisting of aryl, heteroaryl, and aralkyl and $R_{16}R_{17}N$—, each unsubstituted or substituted;
$R_2$ is selected from the group consisting of hydrogen and unsubstituted or substituted $C_{1-10}$alkyl;
$R_3$ is selected from the group consisting of hydrogen, halo, halo$C_{1-10}$alkyl, perhalo$C_{1-10}$alkyl, amino, cyano, nitro, hydroxy, thio, $C_{1-20}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted;
each $R_4$ is independently selected from the group consisting of hydrogen, halo, nitro, halo$C_{1-10}$alkyl, perhalo$C_{1-10}$alkyl, amino, cyano, hydroxy, thio, $C_{1-10}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted, or wherein $R_3$ and an adjacent $R_4$ together form a fused unsubstituted or substituted 5 or 6 membered cycloalkyl, aryl or heteroaryl ring;
$R_{16}$ and $R_{17}$ are each independently $C_{3-12}$cycloalkyl, aryl, heteroaryl, $C_{1-10}$alkyl, each unsubstituted or substituted, or $R_{16}$ and $R_{17}$ together with the nitrogen atom to which they are attached form an unsubstituted or substituted 4, 5 or 6 membered ring; and
$R_{18}$ is selected from the group consisting of $C_{1-10}$alkyl, aralkyl, and heterocycloalkyl, each substituted or unsubstituted; and
m is 0, 1, 2, 3 or 4.

4. The compound of claim 3 comprising the Formula Ic:

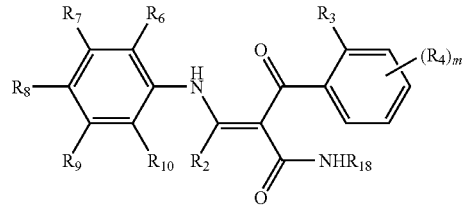

or a pharmaceutically acceptable salt thereof, wherein:
$R_2$ is selected from the group consisting of hydrogen, methyl and ethyl;
$R_3$ is selected from the group consisting of hydrogen, halo, halo$C_{1-10}$alkyl, perhalo$C_{1-10}$alkyl, amino, cyano, nitro, hydroxy, thio, $C_{1-20}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted;

each $R_4$ is independently selected from the group consisting of hydrogen, halo, nitro, halo$C_{1-10}$alkyl, perhalo$C_{1-10}$alkyl, amino, cyano, hydroxy, thio, $C_{1-20}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted, or wherein $R_3$ and an adjacent $R_4$ together form a fused unsubstituted or substituted 5 or 6 membered cycloalkyl, aryl or heteroaryl ring;

$R_6$, $R_7$, $R_8$, $R_9$ and $R_{10}$ are each independently selected from the group consisting of hydrogen, halo, $C_{1-10}$alkyl, $C_{2-10}$alkynyl, $C_{1-10}$alkoxy, aralkyl, cycloalkyl, aryl$C_{1-10}$alkyl and heteroaryl$C_{1-10}$alkyl; or $R_6$ and $R_7$, or $R_7$ and $R_8$, or $R_8$ and $R_9$, or $R_9$ and $R_{10}$ are taken together with the carbon atoms to which they are attached to form an unsubstituted or substituted fused 5 or 6 membered saturated, partially unsaturated ring, aryl or heteroaryl;

$R_{18}$ is selected from the group consisting of $C_{1-10}$alkyl, aralkyl, and heterocycloalky, each unsubstituted or substituted; and m is 0, 1, 2, 3 or 4.

5. The compound of claim 1 comprising the Formula II:

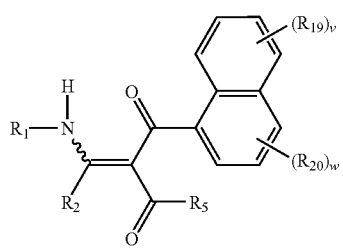

II or a pharmaceutically acceptable salt thereof, wherein:
$R_1$ is selected from the group consisting of aryl, heteroaryl and aralkyl, each unsubstituted or substituted;
$R_2$ is selected from the group consisting of hydrogen and unsubstituted or substituted $C_{1-10}$alkyl;
$R_5$ is selected from the group consisting of —$NH_2$, $C_{1-10}$alkylamino, di($C_{1-10}$)alkylamino and aryl, each unsubstituted or substituted;
$R_{19}$ and $R_{20}$ are each independently selected from the group consisting of halo, cyano, nitro, halo($C_{1-10}$)alkyl, perhalo($C_{1-5}$)alkyl, aryl, heteroaryl, cycloalkyl, $C_{1-10}$alkyl, aryl($C_{1-10}$)alkyl, cycloalkyl($C_{1-10}$)alkyl, hydroxy($C_{1-10}$)alkyl, amino($C_{1-10}$)alkyl, alkoxy($C_{1-10}$)alkyl, amino, hydroxyl, thio, $C_{1-10}$alkoxy and $C_{1-10}$alkylthiol; and
v and w independently are 0, 1, 2 or 3.

6. The compound of claim 1 comprising the Formula III:

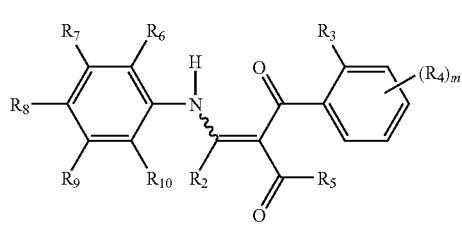

III or a pharmaceutically acceptable salt thereof, wherein:
$R_2$ is selected from the group consisting of hydrogen and unsubstituted or substituted $C_{1-10}$alkyl;
$R_3$ is selected from the group consisting of fluoro, chloro, bromo, iodo, $C_{1-10}$alkoxy, nitro, halo$C_{1-10}$alkyl, perhalo$C_{1-10}$alkyl and unsubstituted or substituted $C_{1-10}$alkyl;
each $R_4$ is independently selected from the group consisting of halogen, nitro, $C_{1-10}$alkyl, $C_{2-10}$alkynyl, $C_{1-10}$alkoxy, aralkyl, aryl, heteroaryl, cycloalkyl and heterocycloalkyl, each unsubstituted or substituted, or wherein $R_3$ and an adjacent $R_4$ together form a fused unsubstituted or substituted 5 or 6 membered cycloalkyl, aryl or heteroaryl ring;
$R_5$ is selected from the group consisting of —$NH_2$, $C_{1-10}$alkylamino, di($C_{1-10}$)alkylamino and aryl, each unsubstituted or substituted;
$R_6$, $R_7$, $R_8$, $R_9$ and $R_{10}$ are each independently selected from the group consisting of hydrogen, halo, $C_{1-10}$alkyl, $C_{2-10}$alkynyl, $C_{1-10}$alkoxy, aralkyl, cycloalkyl, aryl$C_{1-10}$alkyl and heteroaryl$C_{1-10}$alkyl; or $R_6$ and $R_7$, or $R_7$ and $R_8$, or $R_8$ and $R_9$, or $R_9$ and $R_{10}$ are taken together with the carbon atoms to which they are attached to form an unsubstituted or substituted fused 5 or 6 membered saturated, partially unsaturated ring, aryl or heteroaryl; and m is 0, 1, 2, 3 or 4.

7. The compound of claim 1 comprising the Formula IV:

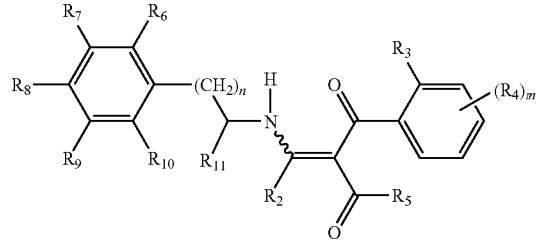

IV or a pharmaceutically acceptable salt thereof, wherein:
$R_2$ is selected from the group consisting of hydrogen and unsubstituted or substituted $C_{1-10}$alkyl;
$R_3$ is selected from the group consisting of fluoro, chloro, bromo, iodo, $C_{1-10}$alkoxy, nitro, halo$C_{1-10}$alkyl, perhalo$C_{1-10}$alkyl and unsubstituted or substituted $C_{1-10}$alkyl;
each $R_4$ is independently selected from the group consisting of halogen, nitro, $C_{1-10}$alkyl, $C_{2-10}$alkynyl, $C_{1-10}$alkoxy, aralkyl, aryl, heteroaryl, cycloalkyl and heterocycloalkyl, each unsubstituted or substituted, or wherein $R_3$ and an adjacent $R_4$ together form a fused unsubstituted or substituted 5 or 6 membered cycloalkyl, aryl or heteroaryl ring;
$R_5$ is selected from the group consisting of —$NH_2$, $C_{1-10}$alkylamino, di($C_{1-10}$)alkylamino and aryl, each unsubstituted or substituted;
$R_6$, $R_7$, $R_8$, $R_9$ and $R_{10}$ are each independently selected from the group consisting of hydrogen, halo, $C_{1-10}$alkyl, $C_{2-10}$alkynyl, $C_{1-10}$alkoxy, aralkyl, cycloalkyl, aryl$C_{1-10}$alkyl and heteroaryl$C_{1-10}$alkyl; or $R_6$ and $R_7$, or $R_7$ and $R_8$, or $R_8$ and $R_9$, or $R_9$ and $R_{10}$ are taken together with the carbon atoms to which they are attached to form an unsubstituted or substituted fused 5 or 6 membered saturated, partially unsaturated ring, aryl or heteroaryl;
$R_{11}$ is hydrogen or is an unsubstituted or substituted $C_{1-10}$alkyl;
m is 0, 1, 2, 3 or 4; and
n is 0, 1, 2, 3, 4 or 5.

8. The compound of claim 3 comprising the Formula IVa:

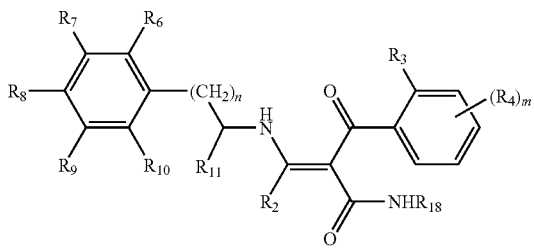

or a pharmaceutically acceptable salt thereof, wherein:
$R_2$ is selected from the group consisting of hydrogen, methyl and ethyl;
$R_3$ is selected from the group consisting of hydrogen, halo, haloC$_{1-10}$alkyl, perhaloC$_{1-10}$alkyl, amino, cyano, nitro, hydroxy, thio, C$_{1-20}$alkyl, C$_{2-10}$alkenyl, C$_{2-10}$alkynyl, cycloalkyl, heterocycloalkyl, aryl, aralkyl, heteroaryl, C$_{1-10}$alkoxy, aryloxy, heteroaryloxy, carbonyl group, sulfonyl group, sulfinyl group, imino group, each unsubstituted or substituted;
each $R_4$ is independently selected from the group consisting of halogen, nitro, C$_{1-10}$alkyl, C$_{2-10}$alkynyl, C$_{1-10}$alkoxy, aralkyl, aryl, heteroaryl, cycloalkyl and heterocycloalkyl, each unsubstituted or substituted, or wherein $R_3$ and an adjacent $R_4$ together form a fused unsubstituted or substituted 5 or 6 membered cycloalkyl, aryl or heteroaryl ring;
$R_6$, $R_7$, $R_8$, $R_9$ and $R_{10}$ are each independently selected from the group consisting of hydrogen, halo, C$_{1-10}$alkyl, C$_{2-10}$alkynyl, C$_{1-10}$alkoxy, aralkyl, cycloalkyl, arylC$_{1-10}$alkyl and heteroarylC$_{1-10}$alkyl; or $R_6$ and $R_7$, or $R_7$ and $R_8$, or $R_8$ and $R_9$, or $R_9$ and $R_{10}$ are taken together with the carbon atoms to which they are attached to form an unsubstituted or substituted fused 5 or 6 membered saturated, partially unsaturated ring, aryl or heteroaryl;
$R_{11}$ is hydrogen or is an unsubstituted or substituted C$_{1-10}$alkyl;
$R_{18}$ is selected from the group consisting of C$_{1-10}$alkyl, arylalkyl and heterocycloalkyl, each unsubstituted or substituted;
m is 0, 1, 2, 3 or 4; and
n is 0, 1, 2, 3, 4 or 5.

9. A compound comprising the Formula V:

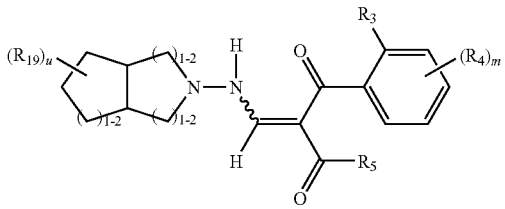

or a pharmaceutically acceptable salt thereof, wherein:
$R_3$ is selected from the group consisting of hydrogen, halo, haloC$_{1-10}$alkyl, perhaloC$_{1-10}$alkyl, amino, cyano, nitro, hydroxy, thio, C$_{1-20}$alkyl, C$_{2-10}$alkenyl, C$_{2-10}$alkynyl, cycloalkyl, heterocycloalkyl, aryl, aralkyl, heteroaryl, C$_{1-10}$alkoxy, aryloxy, heteroaryloxy, carbonyl group, sulfonyl group, sulfinyl group, imino group, each unsubstituted or substituted;
each $R_4$ is independently selected from the group consisting of hydrogen, halo, haloC$_{1-10}$alkyl, perhaloC$_{1-10}$alkyl, amino, cyano, nitro, hydroxy, thio, C$_{1-20}$alkyl, C$_{2-10}$alkenyl, C$_{2-10}$alkynyl, cycloalkyl, heterocycloalkyl, aryl, aralkyl, heteroaryl, C$_{1-10}$alkoxy, aryloxy, heteroaryloxy, carbonyl group, sulfonyl group, sulfinyl group, imino group, each unsubstituted or substituted, or wherein $R_3$ and an adjacent $R_4$ together form a fused unsubstituted or substituted 5 or 6 membered cycloalkyl, aryl or heteroaryl ring;
$R_5$ is selected from the group consisting of alkyl, amino, alkylamino, dialkylamino and aryl, each unsubstituted or substituted;
each $R_{19}$ is independently selected from the group consisting of halogen, C$_{1-10}$alkyl, C$_{2-10}$alkynyl, C$_{1-10}$alkoxy, aralkyl and cycloalkyl, each unsubstituted or substituted;
m is 0, 1, 2, 3 or 4; and
u is 0, 1 or 2.

10. The compound of claim 3 comprising the Formula Va:

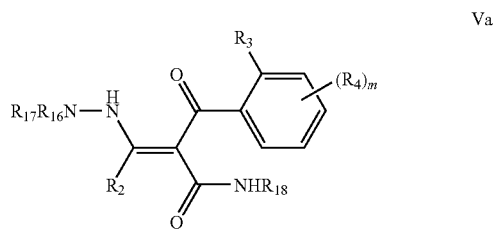

or a pharmaceutically acceptable salt thereof, wherein:
$R_2$ is selected from the group consisting of hydrogen and unsubstituted or substituted C$_{1-10}$alkyl;
$R_3$ is selected from the group consisting of hydrogen, halo, haloC$_{1-10}$alkyl, perhaloC$_{1-10}$alkyl, amino, cyano, nitro, hydroxy, thio, C$_{1-20}$alkyl, C$_{2-10}$alkenyl, C$_{2-10}$alkynyl, cycloalkyl, heterocycloalkyl, aryl, aralkyl, heteroaryl, C$_{1-10}$alkoxy, aryloxy, heteroaryloxy, carbonyl group, sulfonyl group, sulfinyl group, imino group, each unsubstituted or substituted;
each $R_4$ is independently selected from the group consisting of hydrogen, halo, haloC$_{1-10}$alkyl, perhaloC$_{1-10}$alkyl, amino, cyano, nitro, hydroxy, thio, C$_{1-20}$alkyl, C$_{2-10}$alkenyl, C$_{2-10}$alkynyl, cycloalkyl, heterocycloalkyl, aryl, aralkyl, heteroaryl, C$_{1-10}$alkoxy, aryloxy, heteroaryloxy, carbonyl group, sulfonyl group, sulfinyl group, imino group, each unsubstituted or substituted, or wherein $R_3$ and an adjacent $R_4$ together form a fused unsubstituted or substituted 5 or 6 membered cycloalkyl, aryl or heteroaryl ring;
$R_{16}$ and $R_{17}$ are each independently C$_{3-12}$cycloalkyl, aryl, heteroaryl, C$_{1-10}$alkyl, each unsubstituted or substituted, or $R_{16}$ and $R_{17}$ together with the nitrogen atom to which they are attached form an unsubstituted or substituted 4, 5, or 6 membered ring;
$R_{18}$ is selected from the group consisting of C$_{1-10}$alkyl, arylalkyl, and heterocycloalkyl, each unsubstituted or substituted; and
m is 0, 1, 2, 3 or 4.

11. A compound comprising the Formula VI:

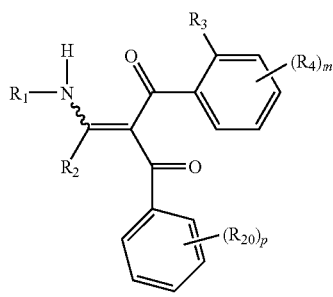

or a pharmaceutically acceptable salt thereof, wherein:
$R_1$ is selected from the group consisting of aryl, heteroaryl, aralkyl and $R_{16}R_{17}N$—, each unsubstituted or substituted;
$R_2$ is selected from the group consisting of hydrogen and unsubstituted or substituted $C_{1-10}$alkyl;
$R_3$ is selected from the group consisting of hydrogen, halo, halo$C_{1-10}$alkyl, perhalo$C_{1-10}$alkyl, amino, cyano, nitro, hydroxy, thio, $C_{1-20}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted;
each $R_4$ is independently selected from the group consisting of halogen, nitro, $C_{1-10}$alkyl, $C_{2-10}$alkynyl, $C_{1-10}$alkoxy, aralkyl, aryl, heteroaryl, cycloalkyl and heterocycloalkyl, each unsubstituted or substituted, or wherein $R_3$ and an adjacent $R_4$ together form a fused unsubstituted or substituted 5 or 6 membered cycloalkyl, aryl or heteroaryl ring;
$R_{16}$ and $R_{17}$ are each independently $C_{3-12}$cycloalkyl, aryl, heteroaryl, $C_{1-10}$alkyl, each unsubstituted or substituted, or $R_{16}$ and $R_{17}$ together with the nitrogen atom to which they are attached form an unsubstituted or substituted 4, 5, or 6 membered ring;
each $R_{20}$ is independently selected from the group consisting of halo, cyano, nitro, halo($C_{1-10}$)alkyl, perhalo($C_{1-5}$)alkyl, aryl, heteroaryl, $C_{1-10}$alkyl, aryl($C_{1-10}$)alkyl, alkoxy($C_{1-10}$)alkyl, amino, hydroxyl, thio and $C_{1-10}$alkoxy and
m and p are each independently 0, 1, 2, 3 or 4.

12. The compound of claim 6, wherein $R_8$ is selected from the group consisting of $C_{1-10}$alkyl, halogen, and $C_{1-10}$alkoxy; and $R_6$, $R_7$, $R_9$ and $R_{10}$ are hydrogen.

13. The compound of claim 12, wherein $R_3$ is selected from the group consisting of methyl, trifluoromethyl and chloro; and m is 0.

14. The compound of claim 1 that is:
2-Chloro-α-[[(4-cyanophenyl)amino]methylene]—N-ethyl-β-oxo-benzenepropanamide;
2-Chloro-N-ethyl-α-[[(4-iodophenyl)amino]methylene]-β-oxo-benzenepropanamide;
2-Chloro-α-[[(4-iodophenyl)amino]methylene]-β-oxo-N-(2-propynyl)-benzenepropanamide;
2-Chloro-α-[[(4-ethynylphenyl)amino]methylene]-β-oxo-N-propyl-benzenepropanamide;
α-[[(4-Ethynylpheny)amino]methylene]-2-methyl-β-oxo-N-propyl-benzenepropanamide;
α-[[(4-Cyanophenyl)amino]methylene]-2-methyl-β-oxo-N-propyl-benzenepropanamide;
α-[[(4-Ethynylphenyeamino]methylene]-2-methyl-β-oxo-N-(2- propynyl)-benzenepropanamide;
2-Chloro-α-[[(4-cyanopheny)amino]methylene]-β-oxo-N-propyl-benzenepropanamide;
2-Chloro-N-ethyl-α[(isoxazolyl-3-amino)methylene]-β-oxo-benzenepropanamide;
α-[(4-EthynylphenyDaminomethylene]-β-oxo-N-propyl-1- naphthalenepropanamide;
2-Chloro-α-[(isoxazolyl-3-amino)methylene]-β-oxo-N-propyl-benzenepropanarnide;
2-Chloro-N-ethyl-β-oxo-α-[(1,2,4-triazolyl-4-amino)methylene]benzene-propanamide;
α-[(4Ethynylpheny)aminomethylene]-β-oxo-N-propyl-1-naphthalenepropanamide;
2-Chloro-N-ethyl-β-oxo-α-[(pyrazinyl)amino]benzenepropanamide;
α-[[(4-chlorophenyeamino]methylene]-N-isopropyl-β-oxobenzenepropanamide;
2-chloro-a-[[(4-chlorophenypamino]methylene]-N-isopropyl-β-oxobenzene-propanamide;
2-chloro-α-[[(4-chlorophenyl)amino]methylene]-N-ethyl-β-oxobenzenepropanamide;
2-chloro-α-[[(4ethoxyphenyl)amino]methylene]-N-ethyl-β-oxobenzene-propanamide;
2-chloro-α-[[(4chlorophenyl)amino]methylene]-N-propyl-β-oxobenzene-propanamide;
2-chloro-α-[[(4-chlorophenypamino]methylene]-N-(1-methylpropyl-β-oxobenzene-propanamide;
2-chloro-N-ethyl-α-[[(α-methyl-4fluorobenzyl)amino]methylene]-β-oxobenzene-propanamide;
2-chloro-N-ethyl-α-[[(α-methylbenzyl)amino]methylene]-β-oxobenzene-propanamide;
2-chloro-α-[[(4-iodophenyl)amino]methylene]-N-methyl-β-oxobenzene-propanamide;
2-chloro-α-[[(4-chlorophenyl)amino]methylene]-N-methyl-β-oxobenzene-propanamide; and 2-chloro-α-[[(4-chlorophenypamino]methylene]-N-(α-methylbenzyl)-β-oxobenzene-propanamide.

15. A pharmaceutical composition, comprising the compound of Formula I:

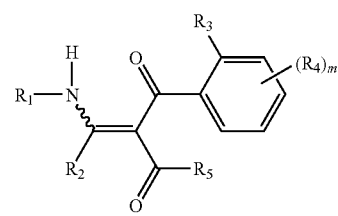

or a pharmaceutically acceptable salt thereof, wherein:
$R_1$ is selected from the group consisting of aryl, heteroaryl, aralkyl and $R_{16}R_{17}N$—, each unsubstituted or substituted;
$R_2$ is selected from the group consisting of hydrogen and unsubstituted or substituted $C_{1-10}$alkyl;
$R_3$ is selected from the group consisting of fluoro, chloro, bromo, iodo, $C_{1-10}$alkoxy, nitro, halo$C_{1-10}$alkyl, perhalo$C_{1-10}$alkyl and unsubstituted or substituted $C_{1-10}$alkyl;
each $R_4$ is independently selected from the group consisting of halogen, nitro, $C_{1-10}$alkyl, $C_{1-10}$alkenyl, $C_{2-10}$alkynyl, $C_{1-10}$alkoxy, aralkyl, aryl, heteroaryl, cycloalkyl and heterocycloalkyl, each unsubstituted or substituted, or wherein $R_3$ and an adjacent $R_4$ together form a fused unsubstituted or substituted 5 or 6 membered cycloalkyl, aryl or heteroaryl ring;

$R_5$ is selected from the group consisting of $C_{1-10}$alkyl, $C_{1-10}$alkoxy, —$NH_2$, $C_{1-10}$alkylamino, di($C_{1-10}$)alkylamino and aryl, each substituted or unsubstituted;

$R_{16}$ and $R_{17}$ are each independently $C_{3-12}$cycloalkyl, aryl, heteroaryl, $C_{1-10}$alkyl, each unsubstituted or substituted, or $R_{16}$ and $R_{17}$ together with the nitrogen atom to which they are attached form an unsubstituted or substituted 4, 5, or 6 membered ring; and m is 0, 1, 2, 3 or 4; with the proviso that when $R_5$ is —OEt, then $R_4$ is not halogen, and the compound of Formula I is not the compounds ethyl α-[(benzyl)aminomethylene]- 2-chloro-β-oxobenzenepropionate and 1-(2,4-dichloro-5-fluorophenye-2-[[(2,4-difluorophenyl)amino]methylene]-1,3-pentanedione; and a pharmaceutically-acceptable carrier selected from the group consisting of excipients and auxiliaries.

16. A pharmaceutical composition comprising the compound of claim 14 and a pharmaceutically-acceptable carrier selected from the group consisting of excipients and auxiliaries.

17. A method for the treatment of a CNS disorder amenable to modulation of the $GABA_A$ receptor complex which comprises administering to a patient in need of such treatment a compound of Formula I:

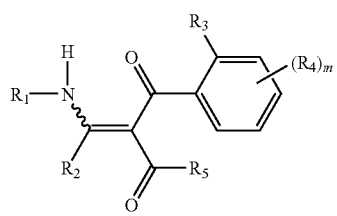

or a pharmaceutically acceptable salt thereof, wherein:

$R_1$ is selected from the group consisting of aryl, heteroaryl, aralkyl and $R_{16}R_{17}N$—, each unsubstituted or substituted;

$R_2$ is selected from the group consisting of hydrogen and unsubstituted or substituted $C_{1-10}$alkyl;

$R_3$ is selected from the group consisting of hydrogen, halo, halo$C_{1-10}$alkyl, perhalo$C_{1-10}$alkyl, amino, cyano, nitro, hydroxy, thio, $C_{1-20}$alkyl, $C_{2-10}$alkenyl, $C_{2-10}$alkyenyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted;

each $R_4$ is independently selected from the group consisting of hydrogen, halo, halo$C_{1-10}$alkyl, perhalo$C_{1-10}$alkyl, amino, cyano nitro, hydroxy, thio, $C_{1-10}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted, or wherein $R_3$ and an adjacent $R_4$ together foam a fused unsubstituted or substituted 5 or 6 membered cycloalkyl, aryl or heteroaryl ring;

$R_5$ is selected from the group consisting of $C_{1-10}$alkyl, $C_{1-10}$alkoxy, —$NH_2$, $C_{1-10}$alkylamino, di($C_{1-10}$)alkylamino and aryl, each substituted or unsubstituted;

$R_{16}$ and $R_{17}$ are each independently $C_{3-12}$cycloalkyl, aryl, heteroaryl, $C_{1-10}$alkyl, each unsubstituted or substituted, or $R_{16}$ and $R_{17}$ together with the nitrogen atom to which they are attached form an unsubstituted or substituted 4, 5, or 6 membered ring; and m is 0, 1, 2, 3 or 4;

wherein said CNS disorder is selected from the group consisting of anxiety disorder, insomnia, major depressive disorder, bipolar disorder, convulsions, withdrawal-induced convulsions from substance abuse, chronic pain, acute pain, neuroses, phobia, panic disorder, generalized anxiety disorder, obsessive-compulsive disorder, post traumatic stress disorder, acute stress disorder, migraine, depression, and epilepsy.

18. A method for the treatment of a sleep disorder involving reduced wakefulness comprising the steps of administering to a patient in need of such a treatment a compound of Formula I:

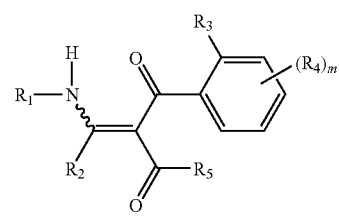

or a pharmaceutically acceptable salt thereof, wherein:

$R_1$ is selected from the group consisting of aryl, heteroaryl, aralkyl and $R_{16}$ $R_{17}N$—, each unsubstituted or substituted;

$R_2$ is selected from the group consisting of hydrogen and unsubstituted or substituted $C_{1-10}$alkyl;

$R_3$ is selected from the group consisting of hydrogen, halo, halo$C_{1-10}$alkyl, perhalo$C_{1-10}$alkyl, amino, cyano, nitro, hydroxy, thio, $C_{1-20}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted;

each $R_4$ is independently selected from the group consisting of hydrogen, halo, halo$C_{1-10}$alkyl, perhalo$C_{1-10}$alkyl, amino, cyano, nitro, hydroxy, thio, $C_{1-20}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted, or wherein $R_3$ and an adjacent $R_4$ together form a fused unsubstituted or substituted 5 or 6 membered cycloalkyl, aryl or heteroaryl ring;

$R_5$ is selected from the group consisting of $C_{1-10}$alkyl, $C_{1-10}$alkoxy, —$NH_2$, $C_{1-10}$alkylamino, di($C_{1-10}$)alkylamino and aryl, each substituted or unsubstituted;

$R_{16}$ and $R_{17}$ are each independently $C_{3-12}$cycloalkyl, aryl, heteroaryl, $C_{1-10}$alkyl, each unsubstituted or substituted, or $R_{16}$ and $R_{17}$ together with the nitrogen atom to which they are attached form an unsubstituted or substituted 4, 5, or 6 membered ring; and m is 0, 1, 2, 3 or 4.

19. The method of claim 18, wherein the sleep disorder involving reduced wakefulness is selected from the group consisting of narcolepsy and idiopathic hypersomnia.

20. The method of claim 17, wherein:

$R_5$ is selected from the group consisting of —$C_{1-10}$alkyl, $CH_3O$—, $C_{3-10}$alkoxy, —$NH_2$, $C_{1-10}$alkylamino, di($C_{1-10}$)alkylamino and aryl, each unsubstituted or substituted.

21. A method for the treatment of a neurodegenerative disorder, which comprises administering to a patient in need of such treatment an effective amount of compound of Formula I:

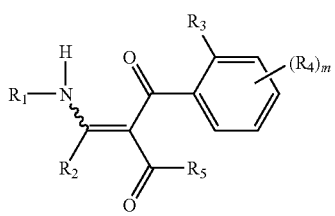

or a pharmaceutically acceptable salt thereof, wherein:

$R_1$ is selected from the group consisting of aryl, heteroaryl, aralkyl and $R_{16}R_{17}N$—, each unsubstituted or substituted;

$R_2$ is selected from the group consisting of hydrogen and unsubstituted or substituted $C_{1-10}$alkyl;

$R_3$ is selected from the group consisting of hydrogen, halo, halo$C_{1-10}$alkyl, perhalo$C_{1-10}$alkyl, amino, cyano, nitro, hydroxy, thio, $C_{1-10}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted;

each $R_4$ is independently selected from the group consisting of hydrogen, halo, halo$C_{1-10}$alkyl, perhalo$C_{1-10}$alkyl, amino, cyano, nitro, hydroxy, thio, $C_{1-20}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted, or wherein $R_3$ and an adjacent $R_4$ together form a fused unsubstituted or substituted 5 or 6 membered cycloalkyl, aryl or heteroaryl ring;

$R_5$ is selected from the group consisting of $C_{1-10}$alkyl, $C_{1-10}$alkoxy, —$NH_2$, $C_{1-10}$alkylamino, di($C_{1-10}$)alkylamino and aryl, each substituted or unsubstituted;

$R_{16}$ and $R_{17}$ are each independently $C_{3-12}$cycloalkyl, aryl, heteroaryl, $C_{1-10}$alkyl, each unsubstituted or substituted, or $R_{16}$ and $R_{17}$ together with the nitrogen atom to which they are attached form an unsubstituted or substituted 4, 5, or 6 membered ring; and m is 0, 1, 2, 3, or 4.

22. A method for the treatment of senile dementia, which comprises administering to a patient in need of such treatment an effective amount of compound of Formula I:

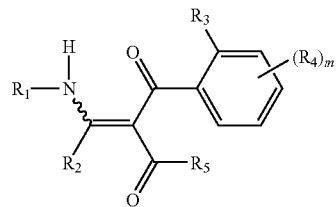

or a pharmaceutically acceptable salt thereof, wherein:

$R_1$ is selected from the group consisting of aryl, heteroaryl, aralkyl and $R_{16}R_{17}N$—, each unsubstituted or substituted;

$R_2$ is selected from the group consisting of hydrogen and unsubstituted or substituted $C_{1-10}$alkyl;

$R_3$ is selected from the group consisting of hydrogen, halo, halo$C_{1-10}$alkyl, perhalo$C_{1-10}$alkyl, amino, cyano, nitro, hydroxy, thio, $C_{2-10}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted;

each $R_4$ is independently selected from the group consisting of hydrogen, halo, halo$C_{1-10}$alkyl, perhalo$C_{1-10}$alkyl, amino, cyano, nitro, hydroxy, thio, $C_{1-20}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted, or wherein $R_3$ and an adjacent $R_4$ together form a fused unsubstituted or substituted 5 or 6 membered cycloalkyl, aryl or heteroaryl ring;

$R_5$ is selected from the group consisting of $C_{1-10}$alkyl, $C_{1-10}$alkoxy, —$NH_2$, $C_{1-10}$alkylamino, di($C_{1-10}$)alkylamino and aryl, each substituted or unsubstituted;

$R_{16}$ and $R_{17}$ are each independently $C_{3-12}$cycloalkyl, aryl, heteroaryl, $C_{1-10}$alkyl, each unsubstituted or substituted, or $R_{16}$ and $R_{17}$ together with the nitrogen atom to which they are attached form an unsubstituted or substituted 4, 5, or 6 membered ring; and m is 0, 1, 2, 3 or 4.

23. A method for the treatment of schizophrenia, which comprises administering to a patient in need of such treatment an effective amount of compound of Formula I:

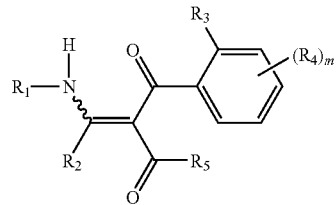

or a pharmaceutically acceptable salt thereof, wherein:

$R_1$ is selected from the group consisting of aryl, heteroaryl, aralkyl and $R_{16}R_{17}N$—, each unsubstituted or substituted;

$R_2$ is selected from the group consisting of hydrogen and unsubstituted or substituted $C_{1-10}$alkyl;

$R_3$ is selected from the group consisting of hydrogen, halo, halo$C_{1-10}$alkyl, perhalo$C_{1-10}$alkyl, amino, cyano, nitro, hydroxy, thio, $C_{1-20}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted;

each $R_4$ is independently selected from the group consisting of hydrogen, halo, halo$C_{1-10}$alkyl, perhalo$C_{1-10}$alkyl, amino, cyano, nitro, hydroxy, thio, $C_{1-20}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted, or wherein $R_3$ and an adjacent $R_4$ together form a fused unsubstituted or substituted 5 or 6 membered cycloalkyl, aryl or heteroaryl ring;

$R_5$ is selected from the group consisting of $C_{1-10}$alkyl, $C_{1-10}$alkoxy, $NH_2$, $C_{1-10}$alkylamino, di($C_{1-10}$)alkylamino and aryl, each substituted or unsubstituted;

$R_{16}$ and $R_{17}$ are each independently $C_{3-12}$cycloalkyl, aryl, heteroaryl, $C_{1-10}$alkyl, each unsubstituted or substituted, or $R_{16}$ and $R_{17}$ together with the nitrogen atom to which they are attached form an unsubstituted or substituted 4, 5, or 6 membered ring; and m is 0, 1, 2, 3 or 4.

24. A method for the treatment of a cognition deficit disorder, which comprises administering to a patient in need of such treatment an effective amount of compound of Formula I:

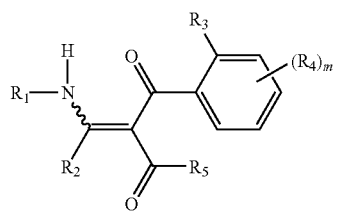

or a pharmaceutically acceptable salt thereof, wherein:
$R_1$ is selected from the group consisting of aryl, heteroaryl, aralkyl and $R_{16}R_{17}N$—, each unsubstituted or substituted;
$R_2$ is selected from the group consisting of hydrogen and unsubstituted or substituted $C_{1-10}$alkyl;
$R_3$ is selected from the group consisting of hydrogen, halo, halo$C_{i1-10}$alkyl, perhalo$C_{1-10}$alkyl, amino, cyano, nitro, hydroxy, thio, $C_{1-20}$alkyl, $C_{1-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted;
each $R_4$ is independently selected from the group consisting of hydrogen, halo, halo$C_{1-10}$alkyl, perhalo$C_{1-10}$alkyl, amino, cyano, nitro, hydroxy, thio, $C_{1-20}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted, or wherein $R_3$ and an adjacent $R_4$ together form a fused unsubstituted or substituted 5 or 6 membered cycloalkyl, aryl or heteroaryl ring;

$R_5$ is selected from the group consisting of $C_{1-10}$alkyl, $C_{1-10}$alkoxy, —$NH_2$, $C_{1-10}$alkylamino, di($C_{1-10}$)alkylamino and aryl, each substituted or unsubstituted;

$R_{16}$ and $R_{17}$ are each independently $C_{3-12}$cycloalkyl, aryl, heteroaryl, $C_{1-10}$alkyl, each unsubstituted or substituted, or $R_{16}$ and $R_{17}$ together with the nitrogen atom to which they are attached form an unsubstituted or substituted 4, 5, or 6 membered ring; and m is 0, 1, 2, 3 or 4.

25. A method for the treatment of mild cognitive impairment, age related cognitive decline, or Alzheimer's disease, which comprises administering to a patient in need of such treatment an effective amount of a compound of Formula I:

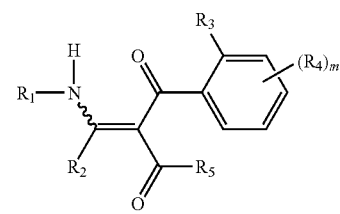

or a pharmaceutically acceptable salt thereof, wherein:
$R_1$ is selected from the group consisting of aryl, heteroaryl, aralkyl and $R_{16}R_{17}N$—, each unsubstituted or substituted;
$R_2$ is selected from the group consisting of hydrogen and unsubstituted or substituted $C_{1-10}$alkyl;
$R_3$ is selected from the group consisting of hydrogen, halo, halo$C_{i1-10}$alkyl, perhalo$C_{1-10}$alkyl, amino, cyano, nitro, hydroxy, thio, $C_{1-10}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted;
each $R_4$ is independently selected from the group consisting of hydrogen, halo, halo$C_{1-10}$alkyl, perhalo$C_{1-10}$alkyl, amino, cyano, nitro, hydroxy, thio, $C_{1-20}$alkyl, $C_{2-10}$alkenyl, $C_{2-10}$alkynyl, cycloalkyl, heterocycloalkyl, aryl, aralkyl, heteroaryl, $C_{1-10}$alkoxy, aryloxy, heteroaryloxy, carbonyl group, sulfonyl group, sulfinyl group, imino group, each unsubstituted or substituted, or wherein $R_3$ and an adjacent $R_4$ together foul a fused unsubstituted or substituted 5 or 6 membered cycloalkyl, aryl or heteroaryl ring;

$R_5$ is selected from the group consisting of $C_{1-10}$alkyl, $C_{1-10}$alkoxy, —$NH_2$, $C_{1-10}$alkylamino, di($C_{1-10}$)alkylamino and aryl, each substituted or unsubstituted;

$R_{16}$ and $R_{17}$ are each independently $C_{3-12}$cycloalkyl, aryl, heteroaryl, $C_{1-10}$alkyl, each unsubstituted or substituted, or $R_{16}$ and $R_{17}$ together with the nitrogen atom to which they are attached form an unsubstituted or substituted 4, 5, or 6 membered ring; and m is 0, 1, 2, 3 or 4.

* * * * *